(12) United States Patent
Boutoussov et al.

(10) Patent No.: US 8,485,818 B2
(45) Date of Patent: *Jul. 16, 2013

(54) FLUID CONTROLLER

(75) Inventors: Dmitri Boutoussov, Dana Point, CA (US); Ioana M. Rizoiu, San Clemente, CA (US)

(73) Assignee: Biolase, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/369,193

(22) Filed: Feb. 8, 2012

(65) Prior Publication Data
US 2012/0136383 A1    May 31, 2012

Related U.S. Application Data

(63) Continuation-in-part of application No. 12/631,642, filed on Dec. 4, 2009, now abandoned.

(51) Int. Cl.
*A61C 1/00* (2006.01)

(52) U.S. Cl.
USPC .................................................. 433/26

(58) Field of Classification Search
USPC .. 433/29, 80, 81, 82, 86, 87, 104, 216; 606/3, 606/10, 13
See application file for complete search history.

(56) References Cited

U.S. PATENT DOCUMENTS

| 3,634,938 A | 1/1972 | Hutchinson |
| 3,640,277 A | 2/1972 | Adelberg |
| 3,679,863 A | 7/1972 | Houldcroft et al. |
| 3,679,998 A | 7/1972 | Dahlinger |
| 3,914,648 A | 10/1975 | Friedman et al. |
| 3,991,296 A | 11/1976 | Kojima et al. |
| 4,005,333 A | 1/1977 | Nichols |
| 4,248,589 A | 2/1981 | Lewis |
| 4,276,518 A | 6/1981 | Ferguson |
| 4,550,275 A | 10/1985 | O'Loughlin |
| 4,668,190 A | 5/1987 | Overmyer |
| 4,718,417 A | 1/1988 | Kittrell et al. |
| 4,724,299 A | 2/1988 | Hammeke |
| 4,826,431 A | 5/1989 | Fujimura et al. |
| 4,862,888 A | 9/1989 | Yessik |
| 4,895,144 A | 1/1990 | Cook et al. |
| 4,908,030 A | 3/1990 | Linkow et al. |
| 4,910,438 A | 3/1990 | Farnsworth |

(Continued)

FOREIGN PATENT DOCUMENTS

| DE | 3911853 A1 | 10/1990 |
| GB | 2352512 A | 1/2001 |
| WO | 2005070129 A2 | 8/2005 |

OTHER PUBLICATIONS

Jones "The Visible Light Spectrum" viewed Jan. 2, 2010, www.about.com (2 pgs.).

(Continued)

*Primary Examiner* — Ralph Lewis
(74) *Attorney, Agent, or Firm* — Jones Day

(57) ABSTRACT

A fluid conditioning system is adapted to condition the fluid used in medical and dental cutting, irrigating, evacuating, cleaning, and drilling operations. The fluid may be conditioned by adding flavors, antiseptics and/or tooth whitening agents such as peroxide, medications, and pigments. In addition to the direct benefits obtained from introduction of these agents, the laser cutting properties may be varied from the selective introduction of the various agents.

24 Claims, 14 Drawing Sheets

U.S. PATENT DOCUMENTS

| | | | |
|---|---|---|---|
| 4,913,142 | A | 4/1990 | Kittrell et al. |
| 4,931,047 | A | 6/1990 | Broadwin et al. |
| 4,941,459 | A | 7/1990 | Mathur |
| 4,960,108 | A | 10/1990 | Reichel et al. |
| 4,985,027 | A | 1/1991 | Dressel |
| 5,086,378 | A | 2/1992 | Prince |
| 5,092,773 | A | 3/1992 | Levy |
| 5,092,864 | A | 3/1992 | Hayes et al. |
| 5,092,865 | A | 3/1992 | Rink |
| 5,102,410 | A | 4/1992 | Dressel |
| 5,128,509 | A | 7/1992 | Black et al. |
| 5,151,029 | A | 9/1992 | Levy |
| 5,199,870 | A | 4/1993 | Steiner et al. |
| 5,221,561 | A | 6/1993 | Flicstein et al. |
| 5,237,331 | A | 8/1993 | Henderson et al. |
| 5,242,454 | A | 9/1993 | Gundlach et al. |
| 5,263,950 | A | 11/1993 | L'Esperance, Jr. |
| 5,267,856 | A | 12/1993 | Wolbarsht et al. |
| 5,306,144 | A | 4/1994 | Hibst et al. |
| 5,313,481 | A | 5/1994 | Cook et al. |
| 5,318,562 | A | 6/1994 | Levy et al. |
| 5,334,019 | A | 8/1994 | Goldsmith et al. |
| 5,374,266 | A | 12/1994 | Kataoka et al. |
| 5,388,988 | A | 2/1995 | Goisser et al. |
| 5,401,171 | A | 3/1995 | Paghdiwala |
| 5,409,376 | A | 4/1995 | Murphy |
| 5,458,594 | A | 10/1995 | Mueller et al. |
| 5,474,449 | A | 12/1995 | Loge et al. |
| 5,479,543 | A | 12/1995 | Black |
| 5,498,935 | A | 3/1996 | McMahan et al. |
| 5,540,683 | A | 7/1996 | Ichikawa et al. |
| 5,552,675 | A | 9/1996 | Lemelson |
| 5,554,172 | A | 9/1996 | Horner et al. |
| 5,611,797 | A | 3/1997 | George |
| 5,694,046 | A | 12/1997 | Hillerich et al. |
| 5,723,864 | A | 3/1998 | Atkinson et al. |
| 5,729,562 | A | 3/1998 | Birx et al. |
| 5,741,247 | A | 4/1998 | Rizoiu et al. |
| 5,755,751 | A | 5/1998 | Eckhouse |
| 5,764,672 | A | 6/1998 | Ukita et al. |
| 5,785,521 | A * | 7/1998 | Rizoiu et al. ............ 433/29 |
| 5,820,627 | A | 10/1998 | Rosen et al. |
| 5,825,958 | A | 10/1998 | Gollihar et al. |
| 5,828,803 | A | 10/1998 | Eckhouse |
| 5,869,805 | A | 2/1999 | Beyer et al. |
| 5,897,509 | A | 4/1999 | Toda et al. |
| 5,971,755 | A | 10/1999 | Liebermann et al. |
| 6,022,316 | A | 2/2000 | Eppstein et al. |
| 6,080,148 | A | 6/2000 | Damasco et al. |
| 6,083,218 | A | 7/2000 | Chou |
| 6,086,366 | A | 7/2000 | Mueller et al. |
| 6,106,516 | A | 8/2000 | Massengill |
| 6,118,521 | A | 9/2000 | Jung et al. |
| 6,183,434 | B1 | 2/2001 | Eppstein |
| 6,223,987 | B1 | 5/2001 | Knowles et al. |
| 6,231,567 | B1 | 5/2001 | Rizoiu et al. |
| 6,254,597 | B1 | 7/2001 | Rizoiu et al. |
| 6,288,499 | B1 | 9/2001 | Rizoiu et al. |
| 6,315,772 | B1 | 11/2001 | Marchitto et al. |
| 6,350,123 | B1 * | 2/2002 | Rizoiu et al. ............ 433/80 |
| 6,389,193 | B1 | 5/2002 | Kimmel et al. |
| 6,449,301 | B1 | 9/2002 | Wu et al. |
| 6,464,689 | B1 | 10/2002 | Qin et al. |
| 6,527,716 | B1 | 3/2003 | Eppstein |
| 6,561,803 | B1 * | 5/2003 | Rizoiu et al. ............ 433/80 |
| 6,610,053 | B1 | 8/2003 | Rizoiu et al. |
| 6,669,685 | B1 | 12/2003 | Rizoiu et al. |
| 6,821,272 | B2 | 11/2004 | Rizoiu et al. |
| 6,853,863 | B2 | 2/2005 | Carter et al. |
| 6,878,899 | B2 | 4/2005 | Smart |
| 6,902,290 | B2 | 6/2005 | Watts et al. |
| 6,960,307 | B2 | 11/2005 | LeClair |
| 6,969,387 | B2 | 11/2005 | Yamamoto |
| 7,108,693 | B2 | 9/2006 | Rizoiu et al. |
| 7,320,594 | B1 * | 1/2008 | Rizoiu et al. ............ 433/29 |
| 7,424,199 | B2 | 9/2008 | Rizoiu et al. |
| 2002/0049432 | A1 | 4/2002 | Mukai |
| 2002/0149324 | A1 | 10/2002 | Rizoiu et al. |
| 2003/0227953 | A1 | 12/2003 | Hsia et al. |
| 2005/0137655 | A1 | 6/2005 | MacFarland |
| 2005/0143792 | A1 | 6/2005 | Jay |
| 2006/0020309 | A1 | 1/2006 | Altshuler et al. |
| 2009/0104580 | A1 | 4/2009 | Rizoiu et al. |

OTHER PUBLICATIONS

European Search Report, EP 05814100, May 3, 2011.

* cited by examiner

| RELATIVE FLOW (CHANNELS OPEN): | |
|---|---|
| A | 1 |
| B | 2 |
| AB | 3 |
| C | 4 |
| AC | 5 |
| BC | 6 |
| ABC | 7 |

FLUID CONTROLLER

CROSS-REFERENCE TO RELATED APPLICATIONS

This application is a continuation-in-part of U.S. application Ser. No. 12/631,642, filed December, 2009 and entitled FLUID CONDITIONING SYSTEM, which is related to U.S. application Ser. No. 11/330,388, filed Jan. 10, 2006 and entitled FLUID CONDITIONING SYSTEM and to U.S. application Ser. No. 11/033,044, filed Jan. 10, 2005 and entitled FLUID CONDITIONING SYSTEM, the entire contents of which are expressly incorporated herein by reference.

BACKGROUND OF THE INVENTION

1. Field of the Invention

The present invention relates generally to medical cutting, irrigating, evacuating, cleaning, and drilling techniques and, more particularly to a device for cutting both hard and soft materials and a system for introducing conditioned fluids into the cutting, irrigating, evacuating, cleaning, and drilling techniques.

2. Description of Related Art

A prior art dental/medical work station 11 is shown in FIG. 1. A vacuum line 12 and an air supply line 13 supply negative and positive pressures, respectively. A water supply line 14 and an electrical outlet 15 supply water and power, respectively. The vacuum line 12, the air supply line 13, the water supply line 14, and the electrical outlet 15 are all connected to the dental/medical (e.g., dental or medical) unit 16.

The dental/medical unit 16 may comprise a dental seat or an operating table, a sink, an overhead light, and other conventional equipment used in dental and medical procedures. The dental/medical unit 16 may provide, for example, water, air, vacuum and/or power to instruments 17. These instruments may include, for example, an electrocauterizer, an electromagnetic energy source, a sonic or ultrasonic source, a mechanical or electrical drill, a mechanical saw, a canal tinder, a syringe, an irrigator and/or an evacuator. Various other types, combinations, and configurations of dental/medical units 16 and subcomponents implementing, for example, an electromagnetic energy device operating with a spray, have also existed in the prior art, many or most of which may have equal applicability to the present invention.

The electromagnetic energy source is typically a laser device coupled with a delivery system. The laser device 18a and delivery system 19a, both shown in phantom, as well as any of the above-mentioned instruments, may be connected directly to the dental/medical unit 16. Alternatively, the laser device 18b and delivery system 19b, both shown in phantom, may be connected directly to the water supply line 14, the air supply line 13, and the electric outlet 15. The mentioned and other instruments 17 may be connected directly to any of the vacuum line 12, the air supply line 13, the water supply line 14, and/or the electrical outlet 15.

The laser device 18 and delivery system 19 may typically comprise an electromagnetic cutter for dental or medical use, although a variety of other types of electromagnetic energy devices operating with fluids (e.g., jets, sprays, mists, or nebulizers) may also be used. An example of one of many varying types of conventional prior art electromagnetic cutters is shown in FIG. 2. According to this example of a prior art apparatus, a fiber guide tube 30, a water line 31, an air line 32, and an air knife line 33 (which supplies pressurized air) my be fed from the dental/medical unit 16 into a hand-held apparatus 34. A cap 35 fits onto the hand-held apparatus 34 and is secured via threads 36. The fiber guide tube 30 abuts within a cylindrical metal piece 37. Another cylindrical metal piece 38 is a part of the cap 35. When the cap 35 is threaded onto the hand-held device 34, the two cylindrical metal tubes 37 and 38 are moved into very close proximity of one another. The pressurized air from the air knife line 33 surrounds and cools a laser beam produced by the laser device as the laser bridges a gap or interface between the two metal cylindrical objects 37 and 38. Air from the air knife line 33 flows out of the two exhausts 39 and 41 after cooling the interface between the two metal cylindrical objects 37 and 38.

Energy from the laser device exits from a fiber guide tube 42 and is applied to a target surface of a treatment/surgical site, which can be within a patient's mouth, for example, according to a predetermined surgical plan. Water from the water line 31 and pressurized air from the air line 32 are forced into the mixing chamber 43 wherein an air and water mixture is formed. The air and water mixture is very turbulent in the mixing chamber 43, and exits the mixing chamber 43 through a mesh screen with small holes 44. The air and water mixture travels along the outside of the fiber guide tube 42, and then leaves the tube 42 and contacts the area of surgery. The air and water spray coming from the tip of the fiber guide tube 42 helps to cool the target surface being cut and to remove materials cut by the laser.

Water is generally used in a variety of laser cutting operations in order to cool the target surface. Additionally, water is used in mechanical drilling operations for cooling the target surface and for removing cut or drilled materials therefrom. Many prior art cutting or drilling systems use a combination of air and water, commonly combined to form a light mist, for cooling a target surface and/or removing cut materials from the target surface.

The use of water in these and other prior art systems has been somewhat successful for purposes of, for example, cooling a target surface or removing debris therefrom. These prior art uses of water in cutting and drilling operations, however, may not have allowed for versatility, outside of, for example, the two functions of cooling and removing debris. In particular, medication treatments, preventative measure applications, and aesthetically pleasing substances, such as flavors or aromas, may have not been possible or used during cutting or drilling operations, including those using systems with water, for example, for cooling or removing debris from a target surface. A conventional drilling operation may benefit from the use of an anesthetic near the drilling operation, for example, but during this conventional drilling operation only water and/or air are often used. In the case of a laser cutting operation, a disinfectant, such as iodine, could be applied to the target surface during drilling to guard against infection, but this additional disinfectant may not be commonly applied during such laser cutting operations. In the case of an oral drilling, cutting, or therapy operation, unpleasant tastes or odors, which may be unpleasing to the patient, may be generated. The common use of only water during this oral procedure does not mask the undesirable taste or odor. A need has thus existed in the prior art for versatility of applications and of treatments during drilling and cutting procedures.

Compressed gases, pressurized air, and electrical motors are commonly used to provide a driving force for mechanical cutting instruments, such as drills, in dentistry and medicine. The compressed gases and pressurized water are subsequently ejected into the atmosphere in close proximity to or inside of the patient's mouth and/or nose or any other treatment/surgical site. The same holds true for electrically driven turbines when a cooling spray (air and water) is typically ejected into the patient's mouth, as well. These ejected fluids commonly contain vaporous elements of tissue fragments, burnt flesh, and ablated or drilled tissue. The odor of these vaporous elements can be quite uncomfortable for the patient, and can increase trauma experienced by the patient during treatment, drilling, or cutting procedures. In such drilling or cutting procedures, a mechanism for masking smells and odors generated from the cutting or drilling may be advantageous.

Another problem exists in the prior art with bacteria growth on surfaces within dental or surgical operating rooms. Interior surfaces of air, vacuum, and water lines of a dental/medical unit, for example, are subject to bacteria growth. In water lines, the bacterial growth is part of the biofilm that may form on an inside of tubing forming a water line. Additionally, the air and water used to cool the tissue being cut or drilled within a patient's mouth are often vaporized into air above a tissue target to some degree or are projected onto a target surface. This vaporized air and water together with projected fluid may condense onto a surface of exposed tissue as well as onto the dental/medical equipment proximal to the treatment site. These surfaces typically are moist, a condition that can promote bacteria growth, which is undesirable. A system for reducing the bacteria growth within air, vacuum, and water lines, and for reducing the bacteria growth resulting from condensation on exterior surfaces (e.g., instruments, devices, or tissue), is needed to reduce sources of contamination of the treatment site as well as contamination of equipment adjacent to the treatment area within a dental/surgical operating room.

SUMMARY OF THE INVENTION

An embodiment of the present invention comprises a fluid conditioning system adaptable to existing medical and dental apparatuses, including those used for cutting, irrigating, evacuating, cleaning, drilling, and therapeutic procedures. The fluid conditioning system may employ flavored fluid in place of or in addition to regular tap water or other types of water (e.g., distilled water, deionized water, sterile water, or water with a controlled number of colony forming units (CFU) per milliliter, and the like), during various clinical operations. In an exemplary case of a laser surgical operation, electromagnetic energy is focused in a direction of tissue to be cut or treated, and a fluid router routes flavored fluid in the same direction. The flavored fluid, which may appeal to the taste buds of a patient undergoing the surgical operation, may include any of a variety of flavors, such as a fruit flavor or a mint flavor. In procedures employing a mist or air spray, scented air may be used to mask a smell of burnt or drilled tissue. The scent may function as an air freshener, even for operations outside of dental applications.

Conditioned fluids may be used for hydrating and cooling a surgical site and/or for removing tissue. The conditioned fluids may include an ionized solution, such as a biocompatible saline solution, and may further include fluids having predetermined densities, specific gravities, pH levels, viscosities, or temperatures, relative to conventional tap water or other types of water. Additionally, the conditioned fluids may include a medication, such as an antibiotic, a steroid, an anesthetic, an anti-inflammatory, an antiseptic or disinfectant (e.g., antibacterial or antiseptic), adrenaline, epinephrine, or an astringent. A typical conditioned fluid may also include vitamins (e.g., vitamin C (ascorbic acid) vitamin E, vitamin $B_{-1}$ (thiamin), $B_{-2}$ (riboflavin), $B_{-3}$ (niacin), $B_{-5}$ (pantothenic acid), $B_{-6}$ (pyridoxal, pyridoxamine, pyridoxine), $B_{-12}$ (cobalamine), biotin or B complex, bioflavonoids, folic acid, vitamin A, vitamin D, vitamin K), aloe vera, natural anti-inflammatory, antioxidant or anti-histamine remedy and other such ingredients and solutions, herbs, remedies or minerals. Still further, the conditioned fluid may include a tooth-whitening agent that is adapted to whiten teeth of patients. The tooth-whitening agent may comprise, for example, a peroxide, such as hydrogen peroxide, urea peroxide, or carbamide peroxide, or any other whitening agent. The tooth-whitening agent may have a viscosity on an order of about 1 to 15 centipoises (cps). In other embodiments, fluid conditioning agents additionally may comprise anticaries, antiplaque, antigingivitis, and/or antitartar agents in fluid or solid (i.e., tablet) form.

Introduction of any of the above-mentioned conditioning agents to conventional fluid such as tap water (or other types of water such as distilled water, deionized water, sterile water, or water with a controlled number of CFU/ml, and the like) used in a cutting, drilling, or therapeutic operation may be controlled by a user input. Thus, for example, a user may adjust a knob or apply pressure to a foot pedal in order to introduce iodine into water before, during (continuously or intermittently), or after a cutting operation (including ablation or vaporization) has been performed. An amount of conditioning may be applied to air, fluid water), and/or jet, spray, mist, nebulizer mist or any other type of such sprays as a function of a position of the foot pedal, for example. A pre-measured or pre-mixed dose of conditioning agents may be introduced via a cartridge according to an embodiment of the present invention. In another embodiment, a cartridge is provided that will mix an appropriate dose of conditioning agent(s) prior to or during a procedure. The cartridge can be implemented, alone or as part of a fluid delivery system, at any location in a path of a fluid source or lines or along an air line or at an air source. The cartridge can also be part of a separate fluid delivery system that provides, for example, sterile and non-sterile fluids to a handpiece (dental, medical regular or medical endoscopic).

According to one broad aspect of the present invention, an apparatus using conditioned fluid to treat a target (e.g., a tissue target), comprises a fluid output pointed in a general direction of an interaction region (e.g., interaction zone), the fluid output being constructed to place conditioned fluid (e.g., conditioned fluid particles) into the interaction region, the interaction region being defined at a location (e.g., volume) adjacent to (e.g., on, or if interaction zone above) the target and the conditioned fluid being compatible with the target, and further comprises an electromagnetic energy source pointed in a direction of the interaction region, the electromagnetic energy source being constructed to deliver into the interaction region a concentration (e.g., a peak concentration) of electromagnetic energy (e.g., that is greater than a concentration of electromagnetic energy delivered onto the target), the electromagnetic energy having a wavelength which is substantially absorbed by the conditioned fluid in the interaction region, wherein the absorption of the electromagnetic energy by the conditioned fluid energizes the fluid causes the fluid to expand) and wherein disruptive forces are imparted onto the target.

The fluid output can be configured to generate a spray (e.g., jet, mist, or nebulizer mist) of atomized particles for placement into a volume of air above the tissue to be cut, and electromagnetic energy from the electromagnetic energy source, for example, a laser beam generated by a laser device, can be focused into the volume of air. The electromagnetic energy has a wavelength, $\lambda$, which may be chosen so that the electromagnetic energy is substantially (e.g., highly) absorbed by the atomized particles in the volume of air. In certain implementations, absorption of the electromagnetic energy by the atomized fluid particles causes the atomized fluid particles to expand, explode and/or to otherwise impart disruptive/removing (e.g., mechanical) forces (e.g., cutting) onto the tissue. In certain implementations, absorption of the electromagnetic energy by the atomized particles causes the atomized particles to expand or explode and disruptive/removing cutting forces are imparted onto the tissue. The expanding or exploding can cause an effect, whereby, at least to some extent, the electromagnetic energy does not directly cut the tissue but, rather, or additionally, expanding or exploding fluid and fluid particles are used, at least in part, to disrupt and/or cut the tissue. In other embodiments, exploding atomized fluid particles may not affect at all, or may affect a percentage but not all of, the cutting of tissue. Examples of such embodiments are disclosed in U.S. application Ser. No. 11/033,032, filed Jan. 10, 2005 and entitled ELECTROMAGNETIC ENERGY DISTRIBUTIONS FOR ELECTROMAGNETICALLY INDUCED DISRUPTIVE CUTTING, the entire contents of which are incorporated herein by reference to the extent compatible and not mutually exclusive. The atomized fluid particles may be formed from fluid conditioned with flavors, scents, ionization, medications, disinfectants (e.g., antibacterial agents and antiseptics), and other agents such as anticaries, antiplaque, antigingivitis, and antitartar agents in fluid or solid (tablet) form, as previously mentioned.

Since the electromagnetic energy is focused directly on the atomized, conditioned fluid particles, the disruptive/cutting forces may be affected by the conditioning of the atomized fluid particles. An efficiency of disruptive and/or cutting can be related (e.g., proportional) to an absorption of the electromagnetic energy by the fluid (e.g., atomized fluid particles). Characteristics of the absorption can be modified by changing a composition of the fluid. For example, introduction of a salt into the fluid (e.g., water) before atomization, thereby creating an ionized solution, may cause changes in absorption—resulting in cutting properties different from those associated with regular water. These different cutting properties, which may be associated with changes in cutting power, may be desirable. A power level of the laser beam may be adjusted to compensate for the ionized fluid particles. Additionally, cutting power may be controlled by pigmenting the atomized fluid particles or by forming (e.g., mixing) the atomized fluid particles at least in part of (e.g., with) carbonated fluid to either enhance or retard absorption of the electromagnetic energy. For example, two sources of fluid may be used, with one of the sources producing fluid containing a pigment or any other particles (e.g., gas from the carbon or other solid particles) and the other producing a fluid not having a pigment or any other particles (e.g., gas from carbon or other solid particles).

Another feature of the present invention places a disinfectant into air, spray, mist, nebulizer mist, jet, or water used for dental or surgical applications. This disinfectant can be periodically routed through air, mist, or fluid (e.g., water) lines to disinfect interior surfaces of these lines. This routing of disinfectant (e.g., antibacterial or antiseptic agents) can be performed, for example, in the context of laser or other treatment or cutting procedures, before or during (continuously or intermittently) procedures, between patient procedures, daily, or at any other predetermined intervals. For example, in certain instances the disinfectant may be applied (e.g., to the target surface) before, during (continuously or intermittently), or immediately following patient procedures. The disinfectant (e.g., antibacterial or antiseptic agents) may consist of or include one or more of chlorine dioxide, stable chlorine dioxide, sodium chlorite ($NaClO_2$), peroxide, hydrogen peroxide, alkaline peroxides, iodine, providone iodine, peracetic acid, acetic acid, chlorite, sodium hypochlorite, citric acid, chlorhexidine gluconate, silver ions, copper ions, equivalents thereof, and combinations thereof.

In accordance with another aspect, disinfectant, such as a liquid in the form of mouthwash, may be used, for example, before, during (continuously or intermittently), or after procedures to decontaminate (e.g., provide an anti-microbial effect within) a surgical tissue site, which can be within a mouth of a patient. The disinfectant also may be used to clean tubes, which may be referred to as lines, that supply air and/or fluid as already described. The disinfectant may comprise, for example, sodium chlorite ($NaClO_2$), chlorine dioxide, or stable chlorine dioxide alone or in combination with ions, such as silver ions. In other embodiments, the disinfectant may comprise, for example, ions, such as silver, copper, or other ions.

According to another feature of the present invention, when disinfectant is routed through the lines before, during, and/or after a medical procedure, the disinfectant stays with the water or mist, as the water or mist becomes airborne and settles (i.e., condenses) on a target tissue site or on surrounding surfaces, which may include adjacent equipment within a dental/medical operating room. Bacteria growth within the lines, and from the condensation, is thereby significantly attenuated, since the disinfectant kills, stops and/or retards bacteria growth inside fluid (e.g., water) lines and/or on any moist surfaces.

The present invention, together with additional features and advantages thereof, may best be understood by reference to the following description taken in connection with the accompanying illustrative drawings.

Any feature or combination of features described herein are included within the scope of the present invention provided that the features included in any such combination are not mutually inconsistent as will be apparent from the context, this specification, and the knowledge of one of ordinary skill in the art. In addition, any feature or combination of features described or referenced may be specifically excluded from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present invention.

Additional advantages and aspects of the present invention are apparent in the following detailed description and claims.

BRIEF DESCRIPTION OF THE DRAWINGS

FIG. 1 illustrates a conventional dental/medical work station;

FIG. 2 is an example of one of many types of conventional optical cutter apparatuses;

FIG. 3 illustrates a dental/medical work station according to an embodiment of the present invention;

FIG. 4 is a schematic block diagram illustrating an electromagnetically induced disruptive cutter using conditioned fluid, according to one embodiment of the present invention;

FIG. 5*a* illustrates one embodiment of an electromagnetically induced disruptive cutter of the present invention;

FIG. 5*b* illustrates another embodiment of an electromagnetically induced disruptive cutter of the present invention;

FIG. 6*a* illustrates a mechanical drilling apparatus according to an implementation of the present invention;

FIG. 6*b* illustrates a syringe according to an implementation of the present invention;

FIG. 7 illustrates a fluid conditioning system according to an embodiment of the present invention;

Figure 22A:
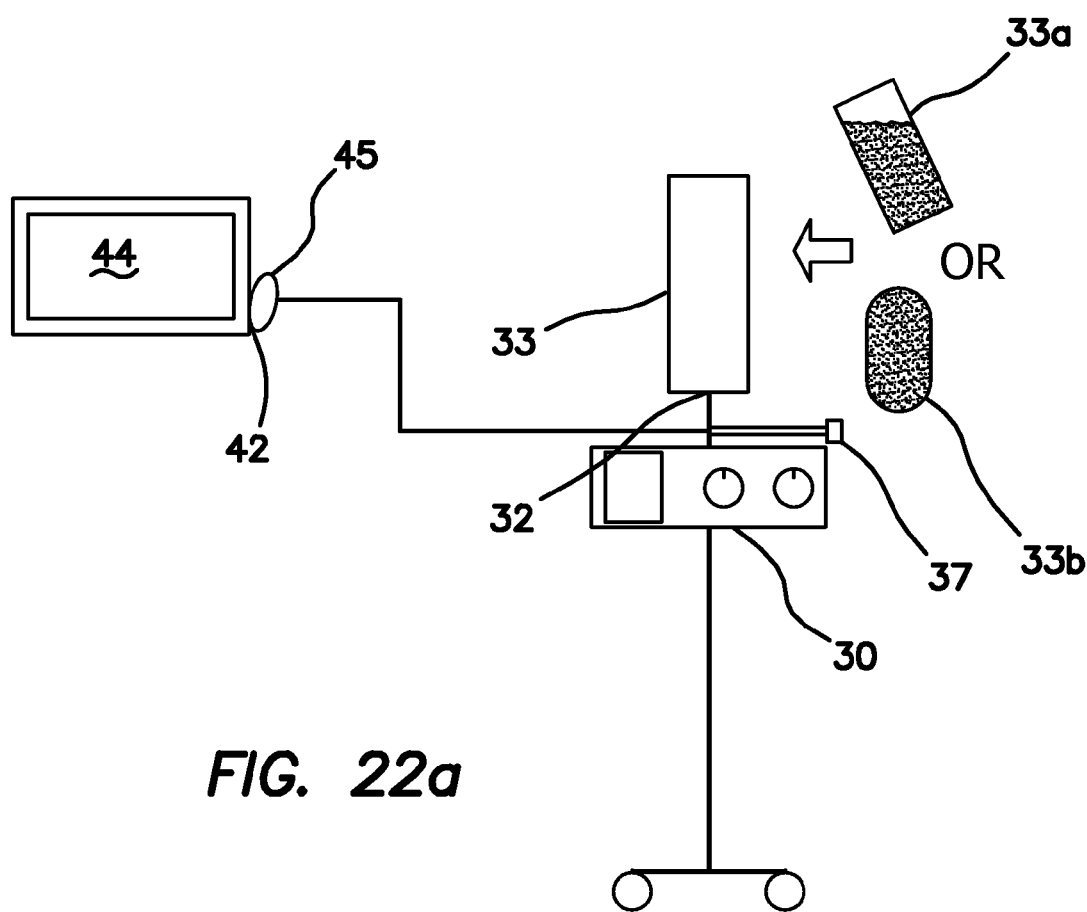
FIG. 22a depicts a sterile water controller adapted for use with an existing Waterlase MBA or Waterlase MD system according to an embodiment of the present invention.
Figure 22B:
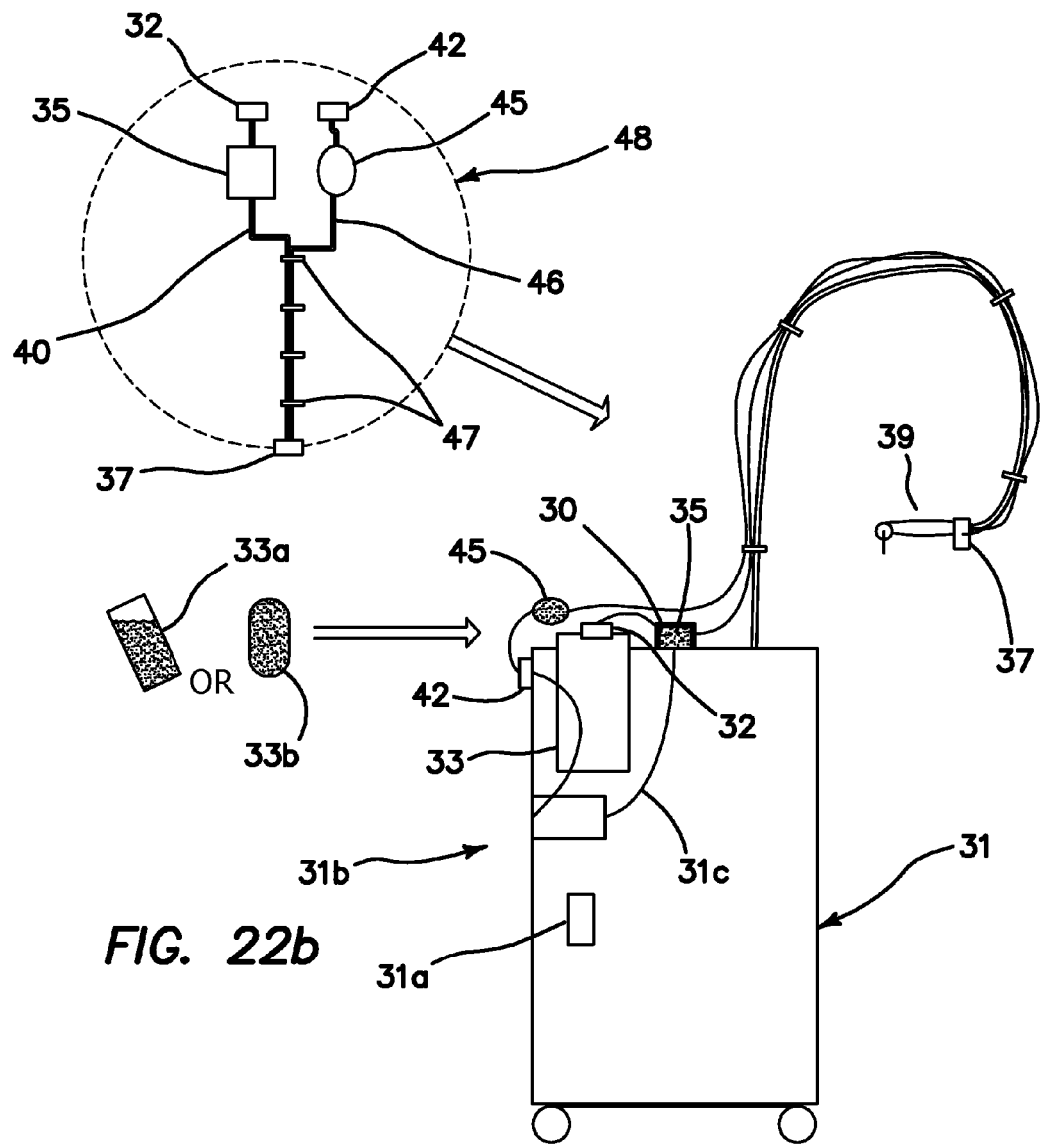
Figure 23:
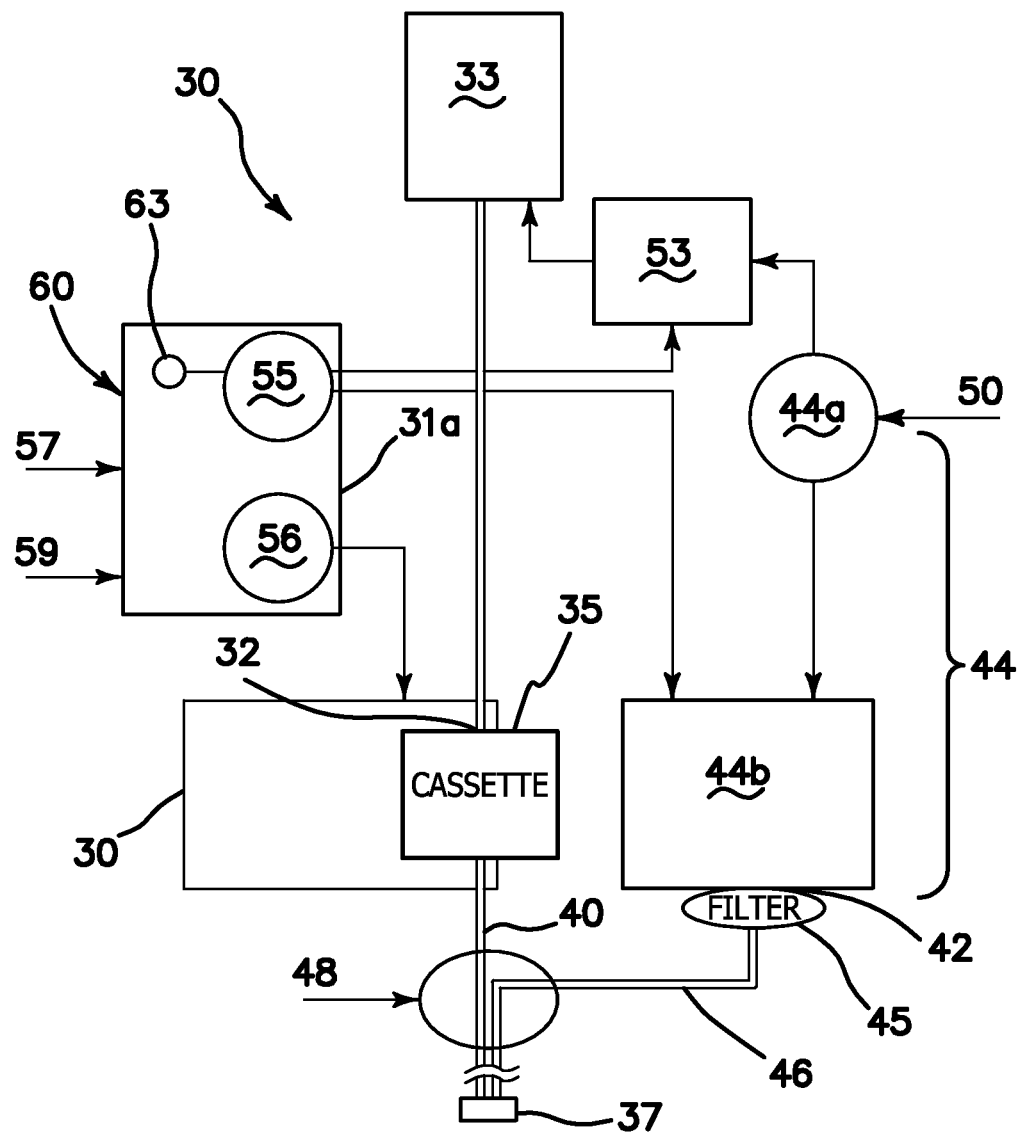
Figure 24:
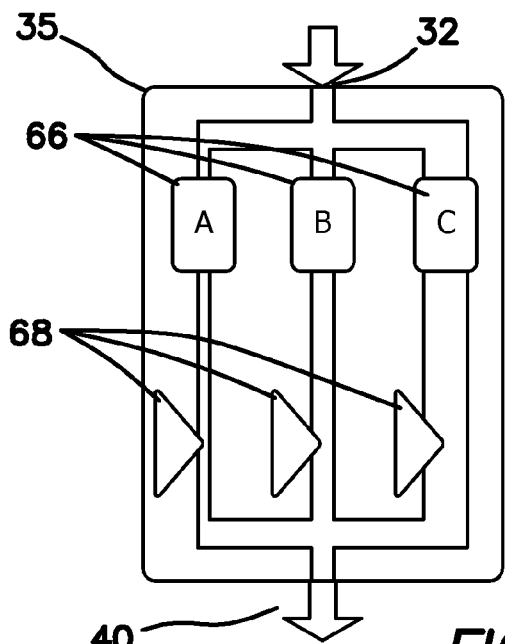
Figure 25:
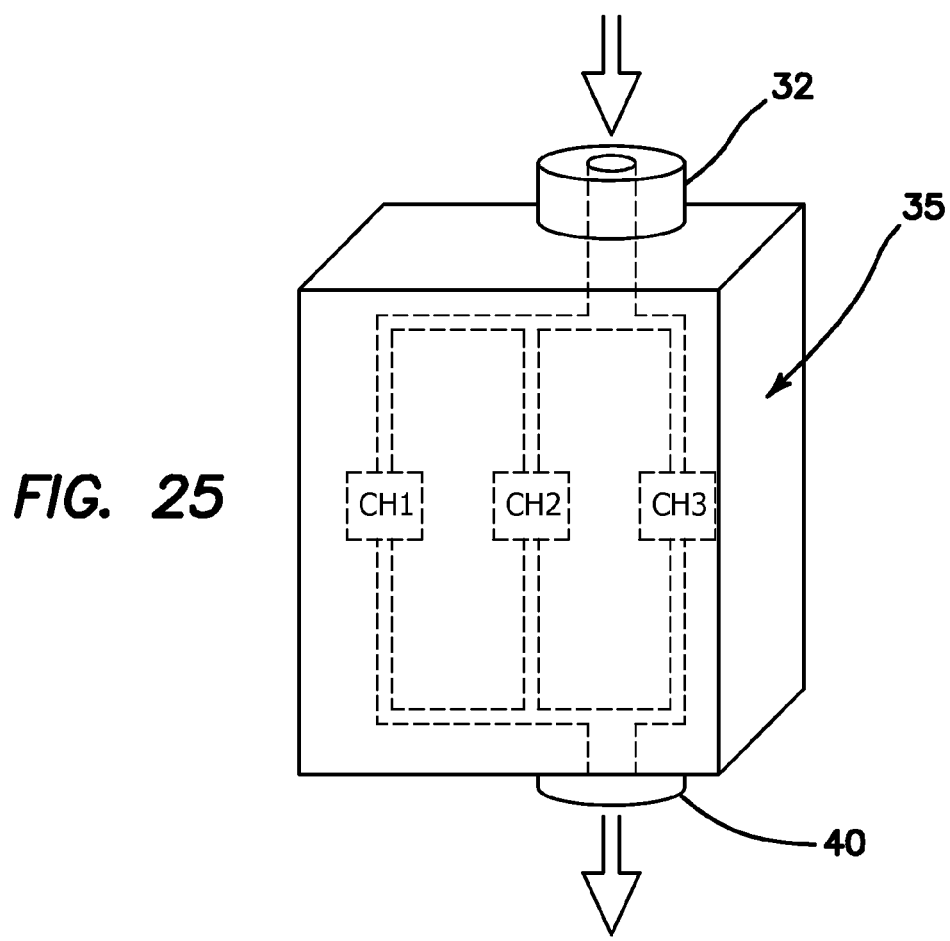

FIG. 22b diagrams a sterile water kit suitable for use with an existing Waterlase MD system according to another embodiment of the present invention;

FIG. 23 is a block diagram of a sterile water controller according to an exemplary arrangement of the present invention;

FIG. 24 is a schematic diagram depicting a sterile water cassette according to an implementation of the present invention; and FIG. 25 is a schematic diagram depicting a sterile water cassette according to another implementation of the present invention.

DETAILED DESCRIPTION OF THE INVENTION

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various devices and techniques that are conventionally used in the art, and only so much of the commonly practiced process steps are included herein as are necessary to provide an understanding of the present invention. The present invention has applicability in the field of laser devices and processes in general. For illustrative purposes, however, the following description pertains to a laser cutting device.

Figure 1:
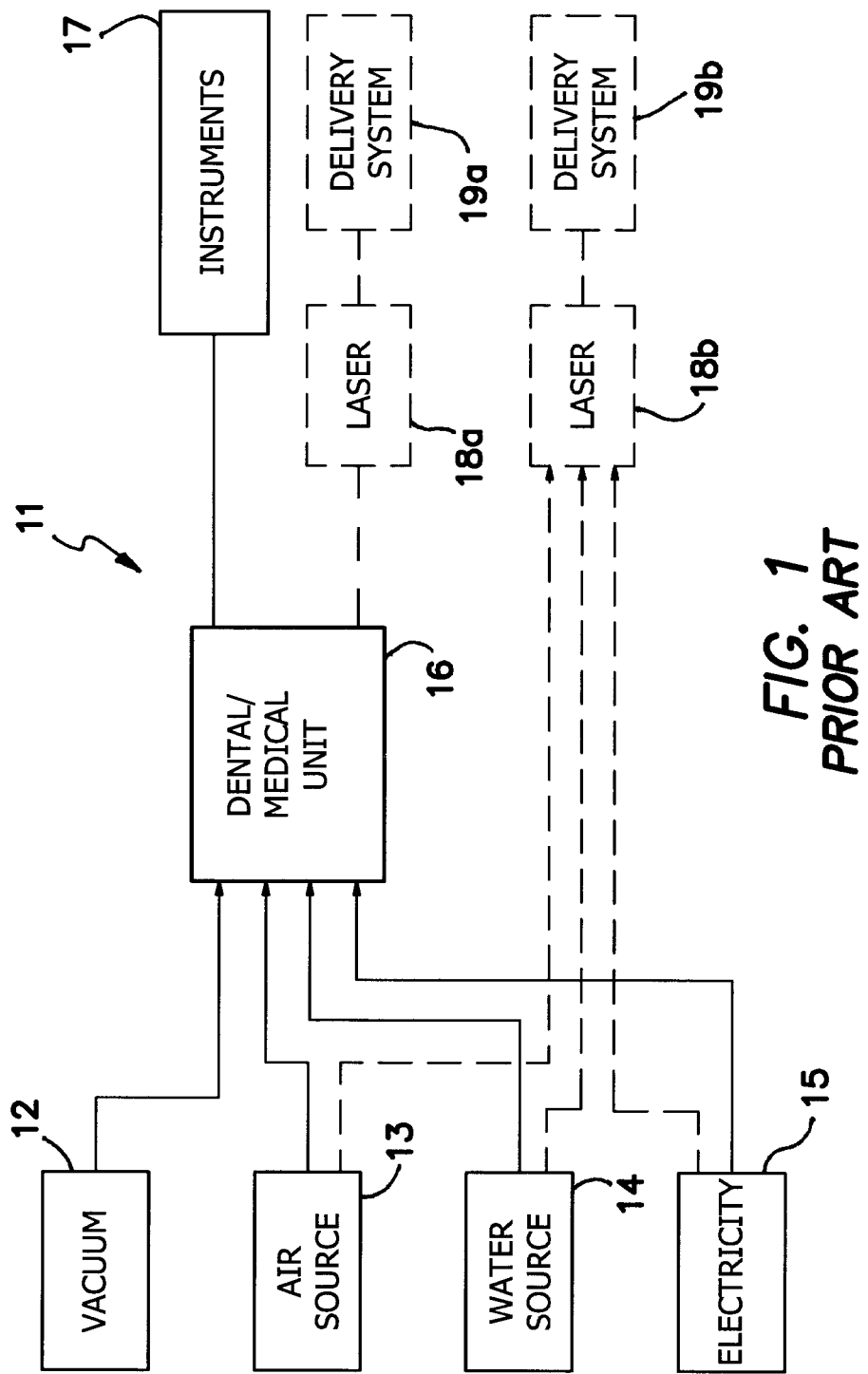
Figure 3:
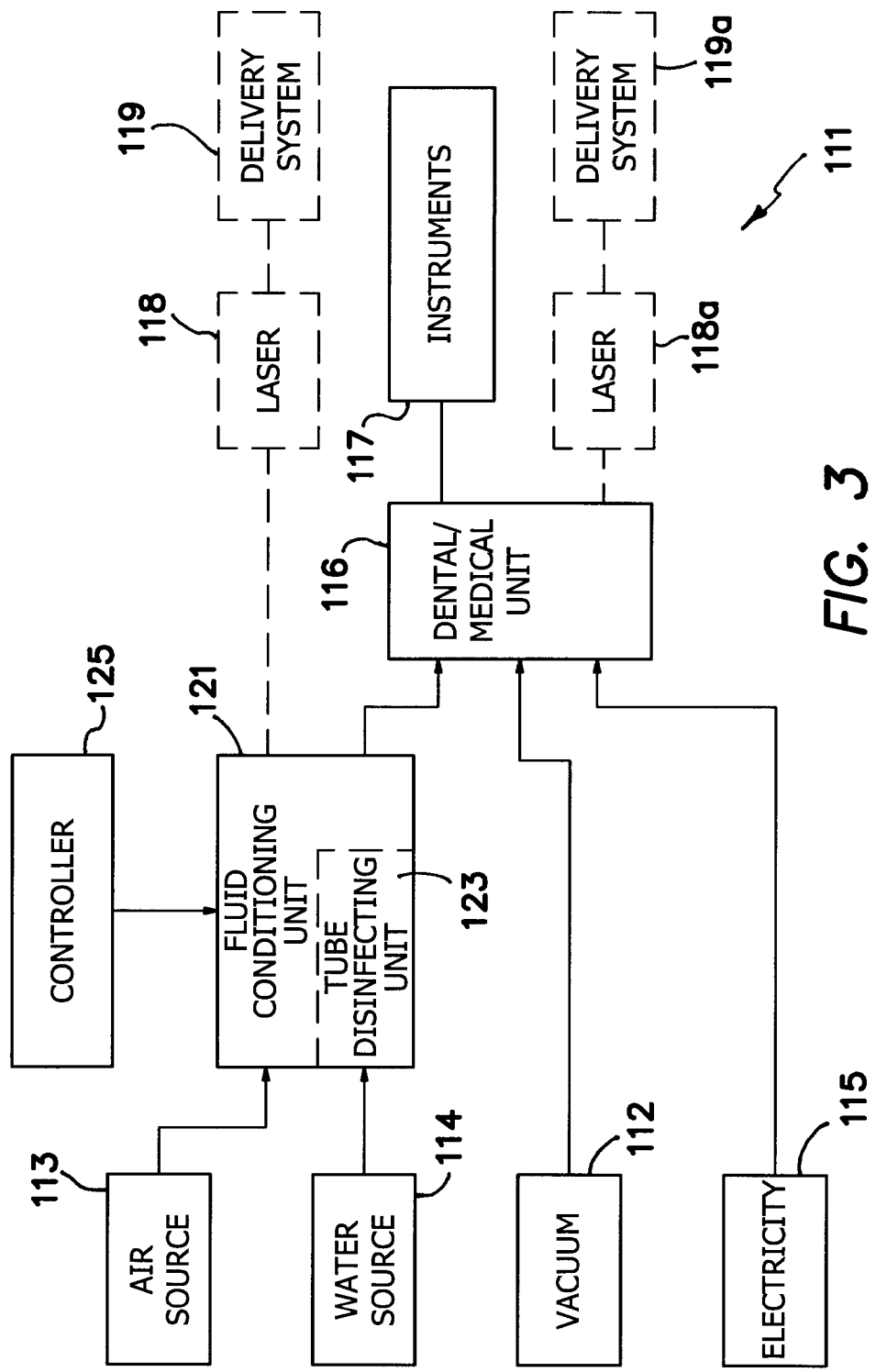

An embodiment of a dental/medical work station 111 according to the present invention is shown in FIG. 3. Elements similar to those shown in FIG. 1 are preceded by a "1". The illustrated embodiment of the dental/medical work station 111 comprises a conventional air line 113 and a conventional biocompatible fluid (e.g., water) line 114 for supplying air and water, respectively. As used herein, the term "water" is intended to encompass various modified embodiments of biocompatible fluids such as distilled water, deionized water, sterile water, tap water, carbonated water, and/or fluid (e.g., water) that has a controlled number of colony forming units (CFU) per milliliter for a bacterial count, and the like. For instance, drinking water is often chemically treated to contain no more than 500 CFU/ml and in some cases between 100 and 200 CFU/ml or even less, such as between 25 and 100 CFU/ml. The embodiment shown in FIG. 3 further comprises a vacuum line 112, an electrical outlet 115, and a dental/medical unit 116. The vacuum line 112 and electrical outlet 115 may supply, respectively, negative air pressure and electricity to the dental/medical (e.g., dental or medical) unit 116, providing functionality similar to that provided by the vacuum line 12 and electrical outlet 15 shown in FIG. 1. The embodiment still further can comprise a fluid conditioning unit 121 and instruments 117. The fluid conditioning unit 121 is typically placed between the dental/medical unit 116 and the instruments 117, but may in other embodiments be placed (1) at, on or in the dental/medical unit 116, (2) upstream of the dental/medical unit 116, (3) downstream of the dental/medical unit 116, or (4) at, on or in one or more of the instruments 117, lasers 118/118a or delivery systems 119/119a According to exemplary implementations of the present invention, one or more of the air line 113 and the biocompatible fluid (e.g., water) line 114 may be provided and fluid conditioning may be introduced into one or more of the provided lines 113 and 114. The line or lines to be provided with fluid conditioning may connect to a fluid conditioning unit 121 and/or may be provided with fluid conditioning using any other structure or method disclosed herein, such as a fluid-conditioning cartridge being coupled to the line or lines to thereby condition fluid passing through the line(s).

The embodiment likewise can comprise a controller 125 that may be configured to accept user inputs, which may control whether air from the air line 113, water from the biocompatible fluid (e.g., water) line 114, or both, are conditioned by the fluid conditioning unit 121. As used herein, mentions of air and/or water are intended to encompass various modified embodiments of the invention, including various biocompatible fluids used with or without the air, and/or water, and including equivalents, substitutions, additives, or permutations thereof. For instance, in certain modified embodiments other biocompatible fluids may be used instead of air and/or water. A variety of agents may be applied to the air or water by the fluid conditioning unit 121, according to a configuration of the controller 125, for example, to thereby condition the air or water, before the air or water is output to the dental/medical unit 116. In one embodiment the air can be supplied from a nitrogen source instead of a regular air line. Flavoring agents and related substances, for example, may be used, as disclosed in 21 C.F.R. Sections 172.510 and 172.515, details of which are incorporated herein by reference. Colors, for example, may also be used for conditioning, such as disclosed in 21 C.F.R. Section 73.1 to Section 73.3126, details of which are incorporated herein by reference.

Similarly to the instruments 17 shown in FIG. 1, the instruments 117 may comprise an electrocauterizer, an electromagnetic energy source, for example, a laser device, a mechanical drill, a sonic/ultrasonic device, a mechanical saw, a canal finder, syringe, an irrigator and/or an evacuator. The above instruments may be incorporated in a handpiece or an endoscope. All of these instruments 117 use air from the air line 113 and/or fluid (e.g., water) from the biocompatible fluid line 114. The biocompatible fluid may or may not be conditioned depending on the configuration of the controller 125. Any of the instruments 117 may alternatively be connected directly to the fluid conditioning unit 121 or directly to any of the air line 113, biocompatible fluid line 114, vacuum line 112, and/or electrical outlet 115. The illustrated embodiment may comprise, for example, a laser device 118 and a delivery system 119 as shown in phantom connected to the fluid conditioning unit 121. The embodiment further may comprise an alternative laser device 118a and an alternative delivery system 119a that may be connected to the dental/medical unit 116 instead of being grouped with the instruments 117. Any of the instruments 117 may be connected directly to any or all of the vacuum line 112, the air line 113, the biocompatible fluid line 114 and the electrical outlet 115 and may have, for example, an independent fluid conditioning unit (e.g., in the form of a cartridge that intercepts and conditions fluid from one or more of the air line 113 and the biocompatible fluid line 114). Instead or additionally, any of these instruments 117 may be connected to the dental/medical unit 116 or the fluid conditioning unit 121, or both.

Figure 4:
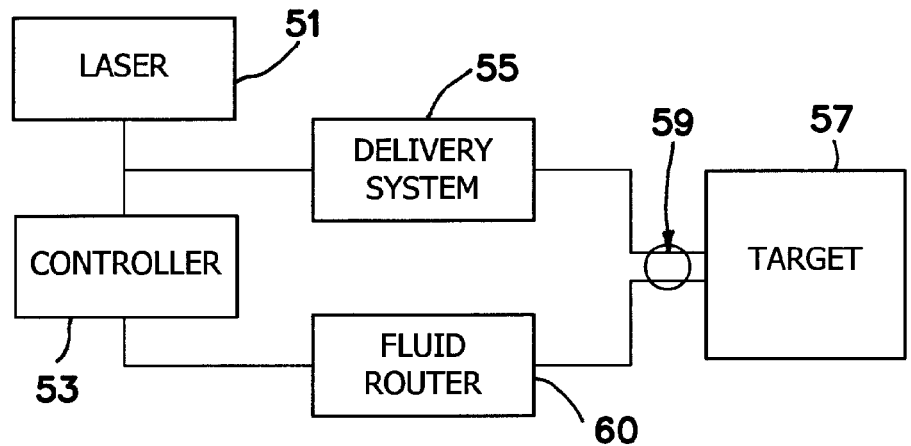

A block diagram shown in FIG. 4 illustrates an exemplary embodiment of a laser device 51 that may be directly coupled with, for example, the air line 113 or with a line supplying another gas such as nitrogen, biocompatible fluid line 114, and electrical outlet 115 of FIG. 3. A separate fluid conditioning system is used in the embodiment illustrated in FIG. 4.

According to the exemplary embodiment shown in FIG. 4, an electromagnetically induced disruptive (e.g., mechanical) cutter is used for cutting and/or coagulation. The laser device 51 (i.e. an electromagnetic cutter energy source) is coupled directly to the electrical outlet 115 (FIG. 3), and is coupled to both a controller 53 and a delivery system 55. The delivery system 55 routes and focuses a laser beam produced by the laser device 51. According to methods associated with a conventional laser system, thermal cutting forces may be imparted onto a target 57 by the laser beam. In contrast, the delivery system 55 of the present invention can comprise a fiberoptic energy guide for routing the laser beam into an interaction zone 59, located above a surface of the target 57. The exemplary embodiment of FIG. 4 further includes a fluid router 60 that may comprise an atomizer for delivering for example user-specified combinations of atomized fluid particles into the interaction zone 59 continuously or intermittently. The atomized fluid particles and/or spray, jet, mist or nebulizer mist) fluids, which may absorb energy from the laser beam, thereby generating disruptive (e.g., cutting) forces as described below, may be conditioned, according to the present invention, and may comprise flavors, scents, medicated substances, disinfectant (e.g., antibacterial or antiseptic agents), saline, tooth-whitening agents, pigment particles or other gaseous or solid particles (e.g., bio-ceramics, bio-glass, medical grade polymers, pyrolitic carbon, encapsulated water based gels, particles or water based gel particles encapsulated into microspheres or microparticles) and other actions or agents such as anticaries, antiplaque, antigingivitis, and antitartar agents in fluid or solid (e.g., tablet) form, as described below.

The delivery system 55 may include a fiberoptic energy guide or equivalent that attaches to the laser device 51 and travels to a desired work site. The fiberoptic energy guide (or waveguide) typically is tong, thin and lightweight, and is easily manipulated. The fiberoptic energy guides can be made of calcium fluoride (CaF), calcium oxide (CaO$_2$), zirconium oxide (ZrO$_2$), zirconium fluoride (Zrf), sapphire, hollow waveguide, liquid core, TeX glass, quartz silica, germanium sulfide, arsenic sulfide, germanium oxide (GeO$_2$), and other materials. Other implementations of the delivery system 55 may include devices comprising mirrors, lenses and other optical components whereby the laser beam travels through a cavity, is directed by various mirrors, and is focused onto the targeted tissue site with specific lenses.

A stream or mist of conditioned fluid may be supplied by the fluid router 60. The controller 53 may control the conditioning of the fluid from the fluid router 60 and specific characteristics of the fluid from the fluid router 60, as well as various operating parameters of the laser device 51

Although the present invention may be used with conventional devices and instruments such as: drills and lasers, for example, an illustrative embodiment includes the above-mentioned electromagnetically induced disruptive cutter. Other embodiments include an electrocauterizer, sonic/ultrasonic device, a syringe, an irrigator, an evacuator, or any air or electrical driver, drilling, filling, or cleaning mechanical instrument.

Figure 10:
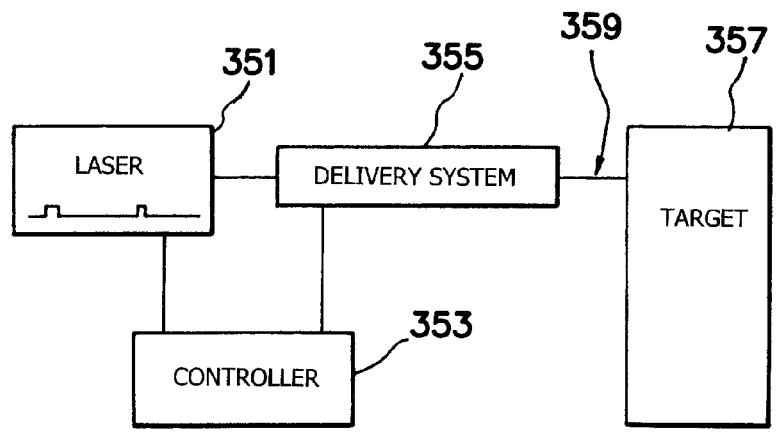
FIG. 10 is a schematic block diagram illustrating an electromagnetically induced disruptive cutter according to an embodiment of the present invention.

FIG. 10 is a block diagram, similar to FIG. 4 as discussed above, illustrating one electromagnetically induced disruptive cutter of the present invention. The block diagram may be identical to that disclosed in FIG. 4 except that the fluid router 60 may not be necessary. As shown in FIG. 10, an electromagnetic energy source, for example, a laser device 351, which may produce a laser beam 350 (FIGS. 15-18) is coupled to both a controller 353 and a delivery system 355. The delivery system 355 imparts disruptive and/or cutting forces onto a target surface 357. In one implementation, the delivery system 355 comprises a fiberoptic guide 23 (FIG. 5b, infra) for routing the laser beam 350 through an optional interaction zone 359 and toward the target surface 357.

Figure 2:
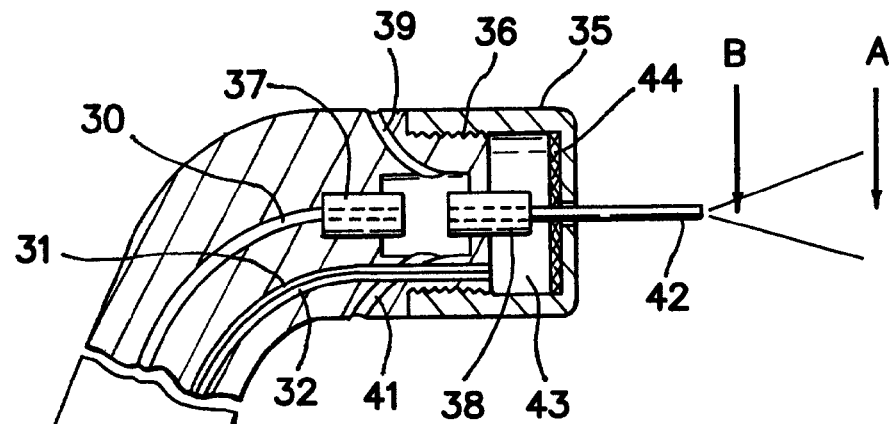
Figure 11:
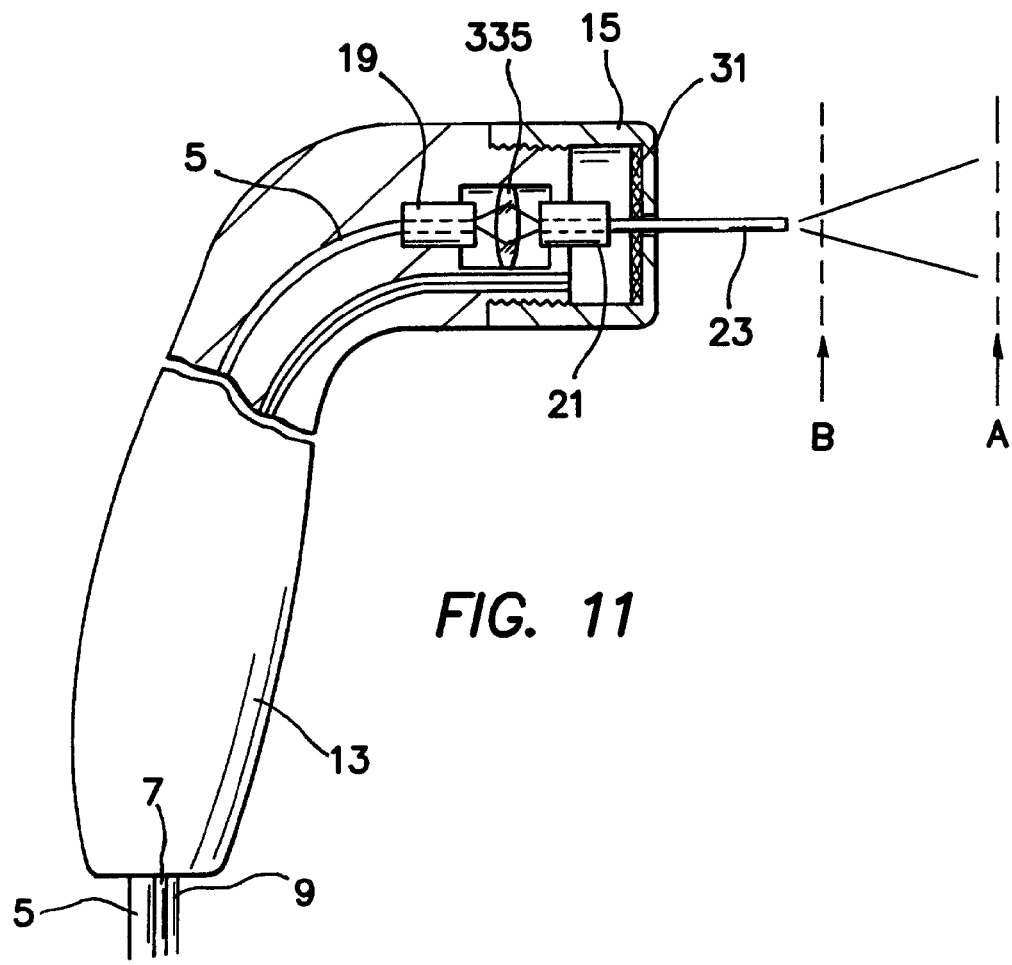
FIG. 11 is an optical cutter having a focusing optic in accordance with an embodiment the present invention.

Referring to FIG. 11, an optical cutter according to one aspect of the present invention is shown, comprising, for example, many conventional elements found in the prior-art electromagnetic cutter illustrated in FIG. 2. The illustrated embodiment comprises a first fiber guide tube 205 that abuts within a cylindrical metal object 219. The first fiber guide tube 205 normally carries laser energy in a typical operating mode. The embodiment further comprises a cap 231, a portion of which comprises another cylindrical metal object 221. The optical cutter illustrated in FIG. 11 comprises a focusing optic 235 disposed between the two metal cylindrical objects 219 and 221. The focusing optic 235 prevents undesired dissipation of laser energy from the first fiber guide tube 205. Although shown coupling the first fiber guide tube 205 with a second fiber guide tube 223 with the first and second fiber guide tubes 205 and 223 having optical axes disposed in a straight line, the focusing optic 235 may be implemented/modified in other embodiments. For example, the focusing optic 235 may be employed to couple fiber guide tubes having non-parallel optical axes (e.g., two fiber guide tubes having perpendicularly aligned optical axes). According to another embodiment, the focusing optic 235 may facilitate rotation of one or both of two fiber guide tubes about their respective optical axes. Yet another embodiment of the focusing optic 235 may comprise one or more of a mirror, a pentaprism, and/or other light directing or transmitting media. Specifically, laser energy from the first fiber guide tube 205 dissipates slightly before being focused by the focusing optic 235. The focusing optic 235 focuses laser energy from the first fiber guide tube 205 into the second fiber guide tube 223. Efficient transfer of laser energy from the first fiber guide tube 205 to the second fiber guide tube 223 may vitiate any need for the conventional air knife cooling system 33, 39, 41 of FIG. 2, because inclusion of the focusing optic 235 may result in dissipation of less laser energy than may occur in the absence of a focusing optic. The first fiber guide tube 205 typically comprises a trunk fiberoptic, which can comprise any of the above-noted fiberoptic materials. In modified embodiments, any aspect of the present invention, in addition to being combinable with the embodiment of FIG. 11, may be combined with a structure of a type illustrated in FIG. 2 and various modifications and equivalents thereof.

Intense energy may be emitted from the fiberoptic guide 223 as can be generated from a coherent source, such as a laser device. In an illustrative embodiment, the laser device comprises an erbium, chromium, yttrium, scandium, gallium garnet (Er, Cr:YSGG) solid state laser device, which generates light having a wavelength in a range of 2.70 to 2.80 µm. As presently embodied, this laser device has a wavelength of approximately 2.78 µm. Fluid, which may be emitted intermittently or continuously from a nozzle 71 (FIG. 5b, infra) comprises water in an illustrative embodiment. Other fluids may be used and appropriate wavelengths of an electromagnetic energy source may be selected to allow for high absorption by the fluid or other particles and substances. Other possible laser systems include an erbium, yttrium, scandium, gallium garnet (Er:YSGG) solid state laser device, which generates electromagnetic energy having a wavelength in a range of 2.70 to 2.80 µm; an erbium, yttrium, aluminum garnet (Er:YAG) solid state laser device, which generates electromagnetic energy having a wavelength of 2.94 µm; a chromium, thulium, erbium, yttrium, aluminum garnet (CTE:YAG) solid state laser device, which generates electromagnetic energy having a wavelength of 2.69 µm; an erbium, yttrium orthoaluminate (Er:YALO3) solid state laser device, which generates electromagnetic energy having a wavelength in a range of 2.71 to 2.86 µm; a holmium, yttrium, aluminum garnet (Ho:YAG) solid state laser device, which generates electromagnetic energy having a wavelength of 2.10 µm; a quadrupled neodymium, yttrium, aluminum garnet (quadrupled Nd:YG) solid state laser device, which generates electromagnetic energy having a wavelength of 266 nm; an argon fluoride (ArF) excimer laser device, which generates electromagnetic energy having a wavelength of 193 nm; a xenon chloride (XeCl) excimer laser device, which generates electromagnetic energy having a wavelength of 308 nm; a krypton fluoride (KrF) excimer laser device, which generates electromagnetic energy having a wavelength of 248 nm; and a carbon dioxide ($CO_2$) laser device, which generates electromagnetic energy having a wavelength in a range of 9.0 to 10.6 µm.

The delivery system 355 of FIG. 10 can further comprise a fluid output, which may or may not differ from the fluid router 60 of FIG. 4. In exemplary embodiments implementing a fluid output, water can be chosen as a preferred fluid because of its biocompatibility, abundance, and low cost. The actual fluid used may vary as long as it is properly matched to the wavelength, $\lambda$, of a selected electromagnetic energy source (e.g., a laser device) meaning that the fluid is capable of partially or highly absorbing electromagnetic energy having a wavelength, $\lambda$, of the selected electromagnetic energy source.

In various implementations of the configuration of FIG. 4, the fluid (e.g., fluid particles and/or other substances including, for example, anticaries, antiplaque, antigingivitis, and antitartar agents in fluid or solid (e.g., tablet) form) can be conditioned as already described. For instance, the fluid can be conditioned to be compatible with a surface of the target 57. In one embodiment, the fluid particles comprise water that is conditioned by for example mild chlorination and/or filtering to render the fluid particles compatible (e.g., containing no harmful parasites) with a tooth or soft tissue target surface in a patient's mouth. In other implementations, other types of conditioning may be performed on the fluid as discussed previously. The delivery system 355 can comprise an atomizer, a sprayer, mister or nebulizer mister for delivering user-specified combinations of atomized fluid particles into the interaction zone 359. The controller 353 controls various operating parameters of the laser device 351, and further controls specific characteristics of a user-specified combination of atomized fluid particles output from the delivery system 355, thereby mediating cutting effects on and/or within the target 357.

Figure 5A:
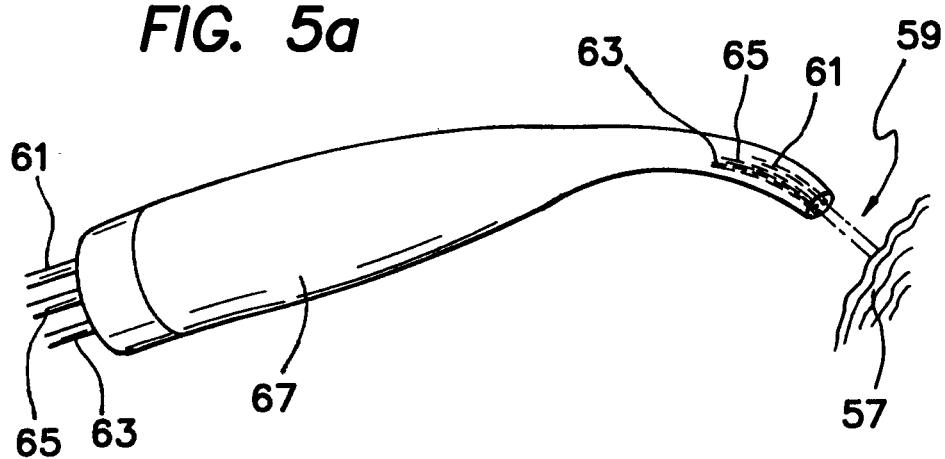

FIG. 5a shows another embodiment of an electromagnetically induced disruptive cutter, in which a fiberoptic guide 61, an air tube 63, and a fluid tube 65, such as a water tube, are placed within a hand-held housing 67. Although a variety of connections are possible, the air tube 63 and water tube 65 can be connected to either the fluid conditioning unit 121 or the dental/medical unit 116 of FIG. 3. The fluid tube 65 can be operated under a relatively low pressure, and the air tube 63 can be operated under a relatively high pressure.

According to one aspect of the present invention, either the air from the air tube 63 or fluid from the fluid tube 65, or both, are selectively conditioned by the fluid conditioning unit 121 (FIG. 3) as controlled by the controller 125. In one implementation, laser energy from the fiberoptic guide 61 focuses onto a combination of air and fluid, from the air tube 63 and the fluid tube 65, at the interaction zone 59. Atomized fluid particles in the air and fluid mixture absorb energy from the laser energy received from the fiberoptic tube 61. The atomized fluid particles may then expand and explode. Explosive forces from these atomized fluid particles can, in certain implementations, impart disruptive (e.g., mechanical) cutting forces onto a surface of the target 57 (FIG. 4).

Turning back to FIG. 2, a conventional optical cutter focuses laser energy onto a target surface at an area A, for example, and in comparison, a typical embodiment of an electromagnetically induced disruptive cutter of the present invention focuses laser energy into an interaction zone B, for example. The conventional optical cutter uses the laser energy directly to cut tissue, and in comparison, the electromagnetically induced disruptive cutter of the present invention uses the laser energy to expand atomized fluid particles to thus impart disruptive cutting forces onto the target surface. The atomized fluid particles and other particles (above, on the surface, or within the target) are heated, expanded, and cooled before or during contacting the target surface or while on or within the target. The prior art optical cutter may use a large amount of laser energy to cut the area of interest, and also may use a large amount of water to both cool this area of interest and remove cut tissue.

In contrast, the electromagnetically induced disruptive cutter of the present invention can use a relatively small amount of fluid (e.g., water) and, further, can use only a small amount of laser energy to expand atomized fluid particles generated from the water. According to the electromagnetically induced disruptive cutter of the present invention, additional water may not be needed to cool an area of surgery, since some of the exploded atomized fluid particles are cooled by exothermic reactions before or while they contact the target surface. Thus, atomized fluid particles of the present invention are heated, expanded, and cooled before contacting the target surface. The electromagnetically induced disruptive cutter of the present invention is thus capable of cutting without charring or discoloration.

Figure 5B:
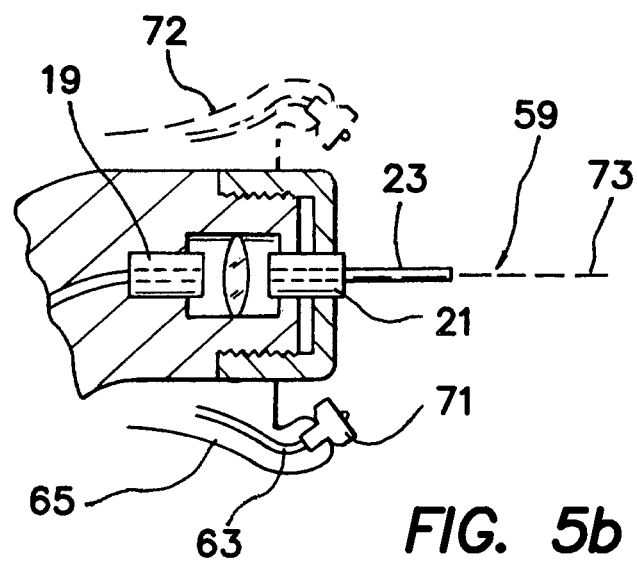

FIG. 5b illustrates another embodiment of the electromagnetically induced disruptive cutter. An atomizer for generating atomized fluid particles comprises a nozzle 71, which may be interchanged with other nozzles (not shown) for obtaining various spatial distributions of the atomized fluid particles, according to the type of cut desired. A second nozzle 72, shown in phantom lines, may also be used. In a simple embodiment, a user controls air and water pressure entering the nozzle 71. The nozzle 71 is thus capable of generating, either intermittently or continuously, many different user-specified combinations of atomized fluid particles and aerosolized sprays. The nozzle 71 is employed to create an engineered combination of small particles of a chosen fluid. The nozzle 71 may comprise several different designs including liquid only, air blast, air assist, swirl, solid cone, etc. When fluid exits the nozzle 71 at a given pressure and rate, the fluid may be transformed into particles of user-controllable sizes, velocities, and spatial distributions. A cone angle may be controlled, for example, by changing a physical structure of the nozzle 71. As another example, various nozzles 71 may be interchangeably placed on the electromagnetically induced disruptive cutter. Alternatively, a physical structure of a single nozzle 71 may be changed.

The fiberoptic guide 23 (FIG. 5b) may emit electromagnetic energy having an optical energy distribution that may be useful for achieving or maximizing a cutting effect of an electromagnetic energy source, such as a laser device, directed toward a target surface. Ablating effects and/or the cutting effect created by the electromagnetic energy may occur on or at the target surface, within the target surface, and/or above the target surface. For instance, using desired optical energy distributions, it is possible to disrupt a target surface by directing electromagnetic energy toward the target surface so that a portion of the electromagnetic energy is absorbed by fluid. The fluid absorbing the electromagnetic energy may be on the target surface, within the target surface, above the target surface, or a combination thereof.

In certain embodiments, the fluid absorbing the electromagnetic energy may comprise water and/or may comprise hydroxyl (e.g., hydroxylapatite). When the fluid comprises hydroxyl and/or water, which may highly absorb the electromagnetic energy, molecules within the fluid may begin to vibrate. As the molecules vibrate, the molecules heat and can expand, leading to, for example, thermal cutting with certain output optical energy distributions. Other thermal cutting or thermal effects may occur by absorption of impinging electromagnetic energy by, for example, other molecules of the target surface. Accordingly, the cutting effects from the electromagnetic energy absorption associated with certain output optical energy distributions may be due to thermal properties (e.g., thermal cutting) and/or to absorption of the electromagnetic energy by molecules (e.g., water above, on, or within the target surface) that does not significantly heat the target surface. The use of certain desired optical energy distributions can reduce secondary damage, such as charring or burning, to the target surface in embodiments, for example, wherein cutting is performed in combination with a fluid output and also in other embodiments that do not use a fluid output. Thus, for example, another portion of the cutting effects caused by the electromagnetic energy may be due to thermal energy, and still another portion of the cutting effects may be due to disruptive (e.g., mechanical) forces generated by the molecules absorbing the electromagnetic energy, as described herein.

Not only can cutting effects of an electromagnetically induced disruptive cutter apparatus be facilitated and/or mediated by fluid distributions above the target surface, as disclosed above, but the cutting effects may alternatively or additionally be facilitated and/or mediated by the absorption of electromagnetic energy by fluid on or within the target surface. In one embodiment of the apparatus, the cutting effects are mediated by effects of energy absorption by a combination of fluid located above the target surface, fluid located on the target surface, and/or fluid located in the target surface. In one embodiment, about 25% to 50% of the impinging electromagnetic energy through fluid and fluid particles and impinges on the target surface. A portion of that impinging energy can operate to cut or contribute to disruption and/or cutting of the target surface. In other embodiments about 10% to 25%, 50% to 80%, or 80% to 95% of the impinging energy passes through fluid and fluid particles and impinges onto the target surface. A portion of that impinging energy can operate to cut or contribute to disruption and/or cutting of the target surface.

A filter may also be provided with the apparatus to modify electromagnetic energy transmitted from the electromagnetic energy source so that the target surface is disrupted in a spatially different manner at one or more points in time compared to electromagnetic energy that is transmitted to a surface without a filter. A spatial and/or temporal distribution of electromagnetic energy may be changed in accordance with a spatial and/or temporal composition of the filter. The filter may comprise, for example, fluid; and in one embodiment the filter is a distribution of atomized fluid particles the characteristics (e.g., size, distribution, velocity, composition) of which can be changed spatially over time to vary an amount of electromagnetic energy impinging on the target surface. As one example, a filter can be intermittently placed over a target to vary the intensity of the impinging electromagnetic energy, thereby providing a type of pulsed effect. In such an example, a spray or sprays of fluid (e.g., water) can be intermittently applied to intersect the impinging electromagnetic energy. As another example, the filter can be placed to intersect the impinging energy continuously. In some embodiments, utilization of a filter for cutting of the target surface may be achieved with reduced, or with no, secondary heating/damage that may typically be associated with thermal cutting resulting from use of prior art lasers that do not have a filter. The fluid of the filter can comprise, for example, water. Outputs from the filter, as well as other fluid outputs, energy sources, and other structures and methods disclosed herein, may comprise any of the fluid outputs and other structures/methods described in U.S. Pat. No. 6,231,567, entitled MATERIAL REMOVER AND METHOD, the entire contents of which are incorporated herein by reference to the extent compatible and not mutually exclusive.

In one embodiment, an output optical energy distribution includes a plurality of high-intensity leading micropulses (one of which may assume a maximum value) that impart relatively high peak amounts of energy. The energy is directed toward the target surface to obtain desired disruptive and/or cutting effects. For example, the energy may be directed into atomized fluid particles, as described above, and into fluid (e.g., water and/or hydroxide (OH) molecules) present on or in material of the target surface, which, in some instances, can comprise water, to thereby expand the fluid and induce disruptive cutting forces to or a disruption (e.g., mechanical disruption) of the target surface. The output optical energy distribution may also include one or more trailing micropulses after a maximum-valued leading micropulse that may further help with removal of material. According to the present invention, a single large leading micropulse may be generated or, alternatively, two or more large leading micropulses may be generated. In accordance with one aspect of the present invention, relatively steeper slopes of the micropulses and shorter durations of the micropulses may tower an amount of residual heat produced in the material.

The output optical energy distribution may be generated by a flashlamp current generating circuit that is configured to generate a relatively narrow pulse having a duration on an order of 0.25 to 300 μs. Diode pumping technology, for example, also may be used to generate the output optical energy distribution. Additionally, a full-width half-maximum (half-max) value of the optical output energy distribution of the present invention can occur within 30 to 70 μs after pulse onset, for example. For comparison, full-width half-max values of the prior art typically occur within the first 250 to 300 μs after pulse onset. Employing a relatively high pulse repetition frequency that may range, for example, from about 1 Hz to about 100 Hz, and further employing a relatively large initial distribution of optical energy in a leading portion of each pulse of the present invention, can result in relatively efficient disruptive cutting (e.g., mechanical cutting). The output optical energy distributions of the present invention can be adapted for cutting, shaping and removing tissues and materials, and further can be adapted for imparting electromagnetic energy into atomized fluid particles over a target surface, or into other fluid particles located on or within the target surface. The cutting effect obtained by the output optical energy distributions of the present invention can be both clean and powerful and, additionally, can impart consistent cuts or other disruptive forces onto target surfaces.

By controlling characteristics of output optical energy, such as pulse intensity, duration, and number of micropulses, a device of the present invention, for example, an embodiment as illustrated in FIG. 5b, can be adjusted to provide a desired treatment for multiple conditions. In addition, the energy emitted from the devices disclosed herein may be effective to cut a target surface, as discussed above, but may also be effective to remodel a target surface. For example, a surface of a tooth can be remodeled without removing any of the tooth structure. In one embodiment, the output optical energy is selected to have properties that are effective to make a surface of a tooth relatively harder and more resistant to attack from acid or bacteria when compared to a level of resistance extant before treatment with one or more of the devices disclosed herein. By making the tooth physically harder, it may become more difficult for bacteria to damage the tooth. Remodeling energy may be particularly effective to inhibit and/or prevent dental carries. In one embodiment, the output optical energy may include a pulse with a relatively longer duration than the pulse described herein that is used for cutting. The pulse may include a series of steep micropulses, as discussed herein, and a longer trail of micropulses where pulse energy is maintained at a desired level for extended periods of time. In another embodiment, two modes of operation may be utilized, such as, for example, a first pulse as described above with one or more intense micropulses, and a second pulse that has a relatively slower leading and trailing slope. Two mode embodiments may be particularly useful when both cutting and remodeling are desired. Thus, by remodeling a surface of a tooth, including anterior and/or posterior surfaces, the tooth may become harder which may be conducive to preventing tooth decay.

Figure 12:
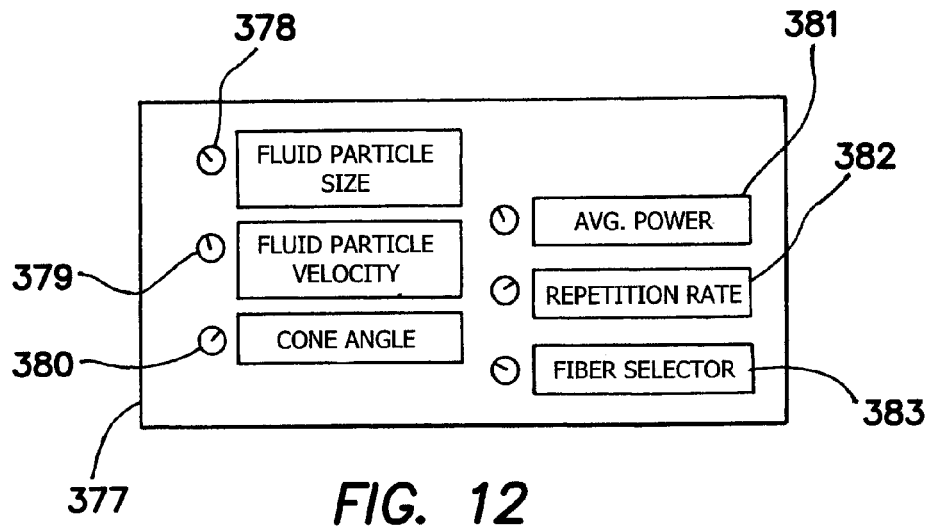
FIG. 12 illustrates a control panel for programming a combination of atomized fluid particles according to an illustrative embodiment of the present invention.

Referring back to the figures, and in particular to FIG. 12, a control panel 377 for allowing user-programmability of atomized fluid particles is illustrated. By changing the pressure and flow rates of fluid, for example, a user can control characteristics of the atomized fluid particles. These characteristics may influence absorption efficiency of laser energy, and subsequent cutting effectiveness of an electromagnetically induced disruptive cutter. The control panel 377 may comprise, for example, a fluid particle size control 378, a fluid particle velocity control 379, a cone angle control 380, an average power control 381, a repetition rate 382, and a fiber selector 383.

Figure 13:
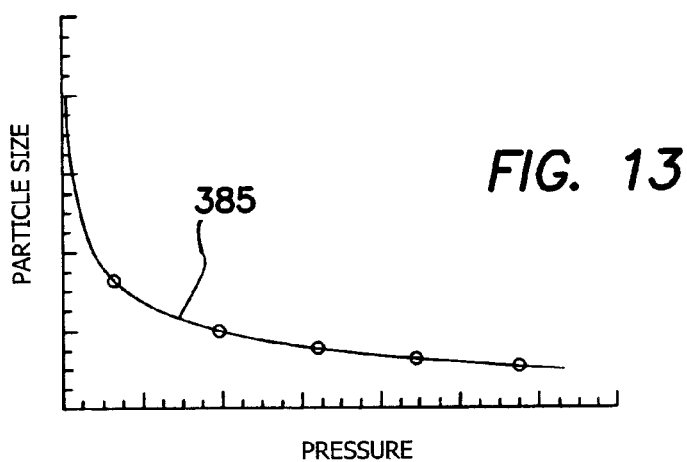
FIG. 13 is a plot of particle size versus fluid pressure in accordance with one implementation of the present invention.
Figure 14:
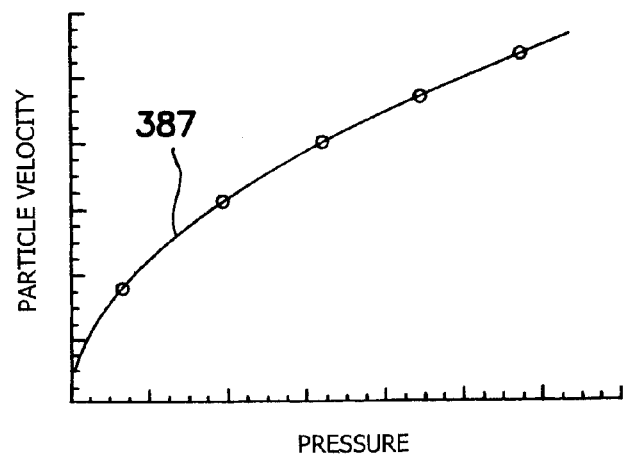
FIG. 14 is a plot of particle velocity versus fluid pressure in accordance with one implementation of the present invention.

FIG. 13 illustrates a plot 385 of mean fluid particle size of atomized fluid particles versus pressure through a nozzle, for example, the nozzle 71 (FIG. 5b), of an embodiment of an electromagnetically induced disruptive cutter. According to the plot 385, when the pressure through the nozzle 71 is increased, the mean fluid particle size of the atomized fluid particles decreases. FIG. 14 is a chart depicting a plot 387 illustrating influence of pressure on mean fluid particle velocity. The plot 387 shows that the mean fluid particle velocity of the atomized fluid particles increases with increasing pressure.

According to one implementation of the present invention, materials can be removed from a target surface, at least in part by disruptive cutting forces instead of by conventional thermal) cutting forces. In such an implementation, electromagnetic energy is used only to induce disruptive forces onto the targeted material. Thus, the atomized fluid particles referred to above act as a medium for transforming electromagnetic energy generated by a laser device into disruptive (e.g., mechanical) energy required to achieve a disruptive cutting effect in accordance with the present invention. The electromagnetic (e.g., laser) energy, itself, may not be directly absorbed by the targeted material. The disruptive (e.g., mechanical) interaction of the present invention can be safer and faster than conventional laser cutting systems. In certain implementations, negative thermal side-effects typically associated with conventional laser cutting systems can be attenuated or eliminated by the present invention.

According to an exemplary operating mode of the electromagnetically induced disruptive cutter, the fiberoptic guide 23 (e.g., FIG. 5b) can be placed into close proximity of a target surface. The fiberoptic guide 23, however, does not actually contact the target surface in this exemplary operating mode. Rather, atomized fluid particles from the nozzle 71 are placed into the interaction zone 59 referenced above in connection with, for example. FIGS. 5a and 5b. A purpose of the fiberoptic guide 23 can thus be to place laser energy deep into a distribution of fluid particles into close proximity of a target surface and into the interaction zone 59.

A feature of the present invention is the formation of the fiberoptic guide 23 of sapphire. Regardless of the composition of the fiberoptic guide 23, however, another feature of the present invention is a cleaning effect on the fiberoptic guide 23 resulting from air and water that may be emitted from the nozzle 71 onto the fiberoptic guide 23. Applicants have found that this cleaning effect is optimal when the nozzle 71 is pointed somewhat directly at the target surface. For example, debris from the disruptive cutting can be removed by a spray from the nozzle 71.

Additionally, applicants have found that pointing the nozzle 71 toward the target surface can enhance cutting efficiency of the present invention. Each atomized fluid particle typically contains a small amount of initial kinetic energy in a direction of the target surface. When electromagnetic energy from the fiberoptic guide 23 contacts an atomized fluid particle, a spherical exterior surface of the fluid particle (e.g., a water particle) acts as a focusing lens to focus the electromagnetic energy into an interior portion of the water particle.

Figure 15:
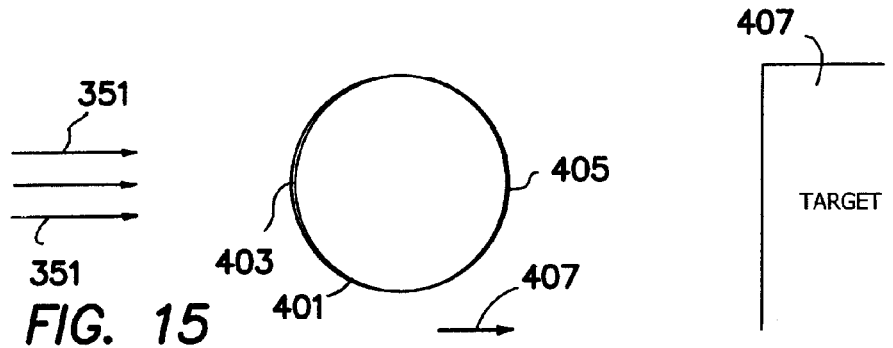
FIG. 15 is a schematic diagram illustrating a fluid particle, a laser beam, and a target surface according to an embodiment of the present invention.

FIG. 15 illustrates a fluid e.g., water) particle 401 having a side with an illuminated surface 403, a shaded side 405, and a particle velocity 408. Electromagnetic energy, which may be a laser beam 350 generated by, for example, a laser device 351 (FIG. 10) focused directly on atomized, conditioned fluid particles as described above, may be absorbed by the fluid particle 401, causing an interior portion of the fluid particle 401 to heat rapidly and to explode. This explosion, which is exothermic, cools remaining portions of the exploded fluid particle 401. Surrounding atomized fluid particles further enhance cooling of portions of the exploded fluid particle 401. The explosion of the fluid particle 401 may generate a pressure wave. This pressure wave, and portions of the exploded fluid particle 401 having increased kinetic energy, are directed toward the target surface 407. These high-energy (e.g., high-velocity) portions of the exploded fluid particle 401, in combination with the pressure wave, may impart strong, concentrated, disruptive (e.g., mechanical) forces onto the target surface 407.

These disruptive forces may cause the target surface 407 to break apart from the material surface through a "chipping away" action. The target surface 407 does not undergo vaporization, disintegration, or charring. The chipping away process (i.e., a cutting process) can be repeated by the present invention until a desired amount of material has been removed from the target surface 407. Unlike prior art systems, certain implementations of the present invention may not require a thin layer of fluid on the target surface 407. In fact, while not wishing to be limited, a thin layer of fluid covering the target surface 407 may in certain implementations interfere with the above-described interaction (e.g., cutting) process. In other implementations, a thin layer of fluid covering the target surface 407 may not interfere with the above-described interaction e.g., cutting) process.

Figure 16:
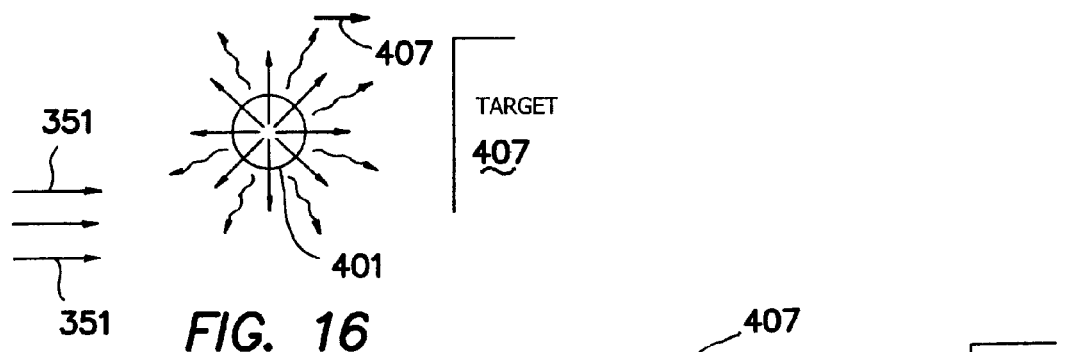
FIG. 16 is a schematic diagram illustrating an "explosive grenade" effect according to an embodiment of the present invention.
Figure 17:
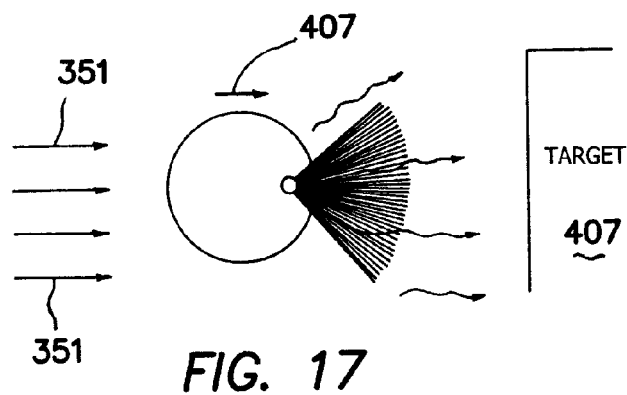
FIG. 17 is a schematic diagram illustrating an "explosive ejection" effect according to an embodiment of the present invention.
Figure 18:
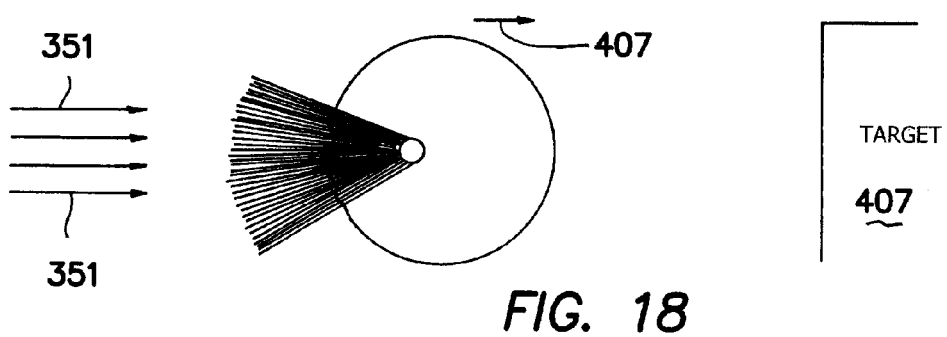
FIG. 18 is a schematic diagram illustrating an "explosive propulsion" effect according to an embodiment of the present invention.

FIGS. 16, 17 and 18 illustrate various types of absorptions of electromagnetic energy by atomized fluid particles according to the present invention. The nozzle 71 (FIG. 5b) can be configured to produce atomized sprays with a range of fluid (e.g., water) particle sizes narrowly distributed about a mean value. A user input device for controlling cutting efficiency or a type of cut may comprise a simple pressure and flow rate gauge or may comprise a control panel 377 as shown in FIG. 12, for example. Receiving a user input for a high resolution cut, for example, may cause the nozzle 71 to generate relatively small fluid particles. Relatively large fluid particles may be generated in response to a user input specifying a low resolution cut. A user input specifying a deep penetration cut may cause the nozzle 71 to generate a relatively low density distribution of fluid particles, and a user input specifying a shallow penetration cut may cause the nozzle 71 to generate a relatively high density distribution of fluid particles. If the user input device comprises the simple pressure and flow rate gauge, then a relatively low density distribution of relatively small fluid particles can be generated in response to a user input specifying a high cutting efficiency. Similarly, a relatively high density distribution of relatively large fluid particles can be generated in response to a user input specifying a low cutting efficiency. Other variations are also possible.

These various parameters can be adjusted according to the type of cut and a type of tissue (e.g., hard tissue and soft tissue) being treated in, for example, dental or medical applications. Hard tissues may include, for example, tooth enamel, tooth dentin, tooth cementum, bone, and cartilage. Soft tissues, which embodiments of the electromagnetically induced disruptive cutter of the present invention also may be adapted to eat, may include skin, mucosa, gingiva, muscle, heart, liver, kidney, brain, eye, and vessels as examples. Other materials appropriate to industrial applications that may be cut may include glass and semiconductor chip surfaces, for example.

A user may also adjust a combination of atomized fluid particles exiting the nozzle 71 to efficiently implement cooling and cleaning of the fiberoptic guide 23 (FIG. 5b). According to an illustrative embodiment, the combination of atomized fluid particles may comprise distribution, velocity, and mean diameter, to effectively cool the fiberoptic guide 23, while simultaneously keeping the fiberoptic guide 23 free of particulate debris, which may be introduced thereon from the target surface 357 (FIG. 10).

Referring again to FIG. 15, electromagnetic energy, for example, the laser beam 350, typically contacts each atomized fluid particle 401 on the illuminated surface 403 and penetrates the atomized fluid particle 401 to a certain depth. The electromagnetic energy, which may be focused into an interior portion of the fluid (e.g., water) particle as described above, may be absorbed by the fluid particle 401, thereby inducing explosive vaporization of the atomized fluid particle 401.

Diameters of atomized fluid particles, for example, the atomized fluid particle 401 (FIGS. 15-18), can be less than, almost equal to, or greater than the wavelength, $\lambda$, of the incident electromagnetic energy corresponding, respectively, to a first, second, and third case of interest, in each of these three cases, a different interaction may occur between the electromagnetic energy and the atomized fluid particle 401. FIG. 16 illustrates the first case, wherein the diameter, d, of the atomized fluid particle 401 is less than the wavelength of the electromagnetic energy ($d<\lambda$). This first case causes a complete volume of fluid inside the fluid particle 401 to absorb the electromagnetic (e.g., laser) energy, thereby inducing explosive vaporization. The fluid particle 401 explodes, ejecting its contents radially. Applicants refer to this phenomenon as an "explosive grenade" effect. As a result of this interaction, radial pressure waves from the explosion are created and projected in a direction of propagation of the electromagnetic energy. The direction of propagation is toward the target surface 407, and in one embodiment, both the electromagnetic (e.g., laser) energy and the atomized fluid particles are traveling substantially in the direction of propagation.

Explosion of the fluid particle 401 produces portions that, acting in combination with the pressure wave, produce a "chipping away" effect of cutting and removing of materials from the target surface 407. Thus, according to the "explosive grenade" effect of the first case as shown in FIG. 16, a relatively small diameter of the fluid particle 401 allows electromagnetic energy from the laser beam 350 to penetrate and to be absorbed violently within an entire volume of the fluid particle 401. Explosion of the fluid particle 401 can be analogized to an exploding grenade, which radially ejects energy and shrapnel. Water content of the fluid particle 401 may be vaporized due to strong absorption within a small volume of fluid, and the pressure waves created during this process produce the cutting process, which may remove material.

FIG. 17 illustrates the second case introduced above, wherein the fluid particle 401 has a diameter, d, approximately equal to the wavelength of the electromagnetic energy ($d\approx\lambda$). According to this second case, an "explosive ejection" effect may be produced, according to which the electromagnetic (e.g., laser energy travels through the fluid particle 401 before becoming absorbed by the fluid therein. Once the electromagnetic energy is absorbed, the shaded side of the fluid particle heats up, and explosive vaporization occurs. In this second case, internal particle fluid is violently ejected through the fluid particle's shaded side, and the ejected fluid moves rapidly with the explosive pressure wave referenced above toward the target surface. As shown in FIG. 17, the electromagnetic (e.g., laser) energy is able to penetrate the fluid particle 401 and to be absorbed within a depth dose to the size of the diameter of the fluid particle 401. A center of explosive vaporization in the second case illustrated in FIG. 17 is closer to the shaded side 405 of the moving fluid particle 401. According to this "explosive ejection" effect shown in FIG. 17, the vaporized fluid is violently ejected through the shaded side of the particle toward the target surface 407.

A third case introduced above and shown in FIG. 18 generates an "explosive propulsion" effect. In this third case, the diameter, d, of the fluid particle is larger than the wavelength of the electromagnetic (e.g., laser) energy (d>λ). The electromagnetic (e.g., laser) energy in this third case, penetrates the fluid particle 401 only a small distance through the illuminated surface 403 causing this illuminated surface 403 to vaporize. The vaporization of the illuminated surface 403 tends to propel a remaining portion of the fluid particle 401 toward the target surface 407. Thus, a portion of mass of the fluid particle 401 gains kinetic energy, thereby propelling a remaining portion of the fluid particle 401 toward the target surface 407 with a high kinetic energy. This high kinetic energy is additive to the initial kinetic energy of the fluid particle 401. The effects shown in FIG. 18 can be visualized as a micro-hydro rocket having a jet tail, which helps to propel the fluid particle 401 with high velocity toward the target surface 407. Exploding vapor on a side having the illuminated surface 403 thus supplements a velocity corresponding to the initial kinetic energy of the fluid particle 401.

Figure 19:
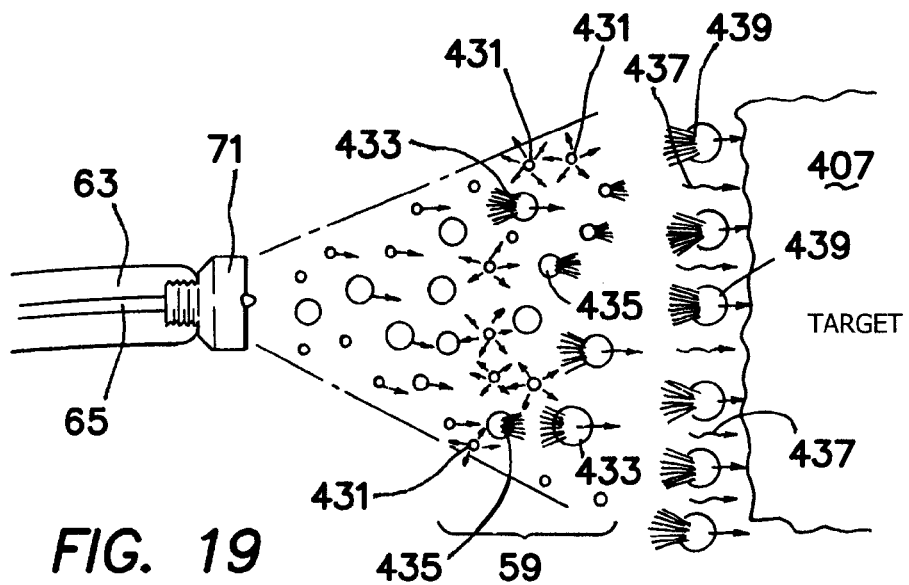
FIG. 19 is a schematic diagram illustrating a combination of FIGS. 16-18.

A combination of FIGS. 16-18 is shown in FIG. 19. The nozzle 71 (see also FIG. 5b) produces a combination of atomized fluid particles that are transported into the interaction zone 59. In some embodiments, the laser beam 350 (FIGS. 15-18) can be focused (intermittently or continuously) on this interaction zone 59. Relatively small fluid particles 431 vaporize according to the explosive grenade effect described above, and relatively large fluid particles 433 explode via the "explosive propulsion" effect likewise described above. As further described above, medium sized fluid particles, having diameters approximately equal to the wavelength of the electromagnetic energy (e.g., the laser beam 350) and shown by the reference number 435, explode via the explosive ejection" effect. Resulting pressure waves 437 and exploded fluid particles 439 impinge upon the target surface 407.

Figure 20:
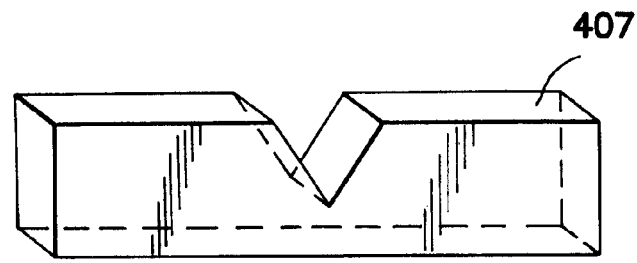
FIG. 20 is a schematic diagram illustrating the "cleanness" of cut obtained by the present invention.
Figure 21:
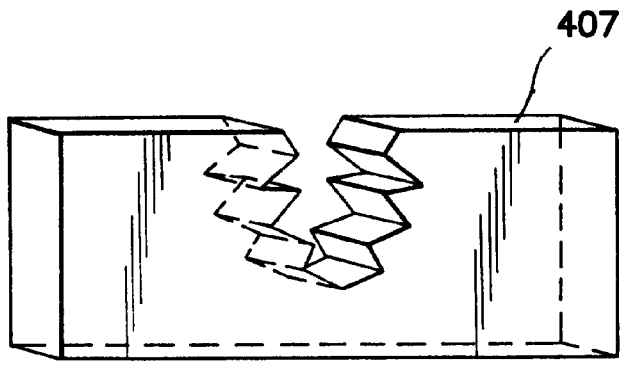
FIG. 21 is a schematic diagram illustrating the roughness of cut obtained by prior art systems.

FIG. 20 illustrates the clean, high resolution cut which can be produced by the electromagnetically induced disruptive (e.g., mechanical) cutter of the present invention. Unlike some cuts of the prior art that may be generated such as shown for example in FIG. 21, the cut of the present invention can be clean and precise. Among other advantages, the cut of the present invention can provide one or more of an ideal bonding surface, accuracy, and attenuation of stress on remaining materials surrounding the cut.

Figure 6A:
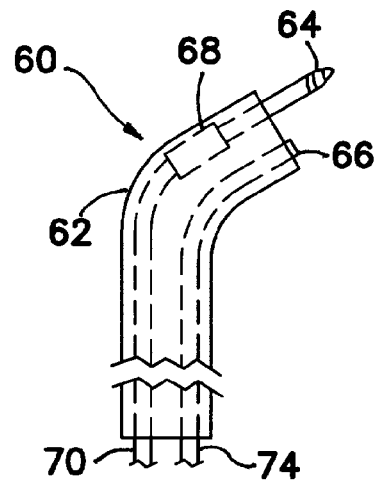

An illustrative embodiment of a structure for light delivery, for example, for delivery of the laser beam 350 (FIGS. 15-18), for medical applications of the present invention is through a fiberoptic conductor, for example, the fiberoptic guide 223 illustrated in FIG. 11, because of its light weight, relatively low cost, and ability to be packaged inside of a handpiece of familiar size and weight to a surgeon, dentist, or clinician. Non-fiberoptic systems may be used in both industrial applications and medical applications, as well. As described above with reference to FIG. 3, the collection of instruments 117 may comprise a mechanical drill. An example of such a mechanical drill 160 is shown in FIG. 6a, comprising a handle 62, a drill bit 64, and a water output 66. The mechanical drill 160 comprises a motor 68, which may be electrically driven, or which may be driven by pressurized air.

When the motor 68 is driven by air, for example, a fluid may enter the mechanical drill 160 through a first supply line 70. Fluid entering through the first supply line 70 passes through the motor 68, which may comprise a turbine, for example, to thereby provide rotational forces to the drill bit 64. A portion of the fluid, which may not appeal to a patient's taste and/or smell, may exit around the drill bit 64, coming into contact with the patient's mouth and/or nose. The majority of the fluid exits back through the first supply line 70.

When the motor is electrically driven, for example, the first supply line 70 provides electric power. A second supply line 74 supplies fluid to a fluid output 66. The water and/or air supplied to the mechanical drill 160 may be selectively conditioned by a fluid conditioning unit, for example, the fluid conditioning unit 121 illustrated in FIG. 3, according to a configuration of a controller, for example, the controller 125 likewise illustrated in FIG. 3.

Figure 6B:
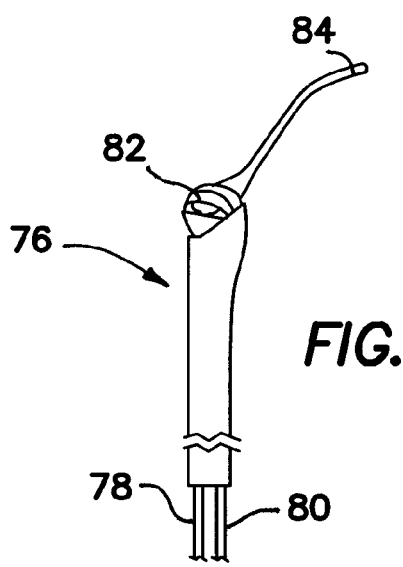

The instruments 117 (FIG. 3) further may comprise a syringe 76 as shown in FIG. 6b. The illustrated embodiment of a syringe 76 comprises an air input line 78 and a water input line 80. A user control 82 is movable between a first position and a second position. The user control 82, when placed into the first position, causes air from the air input line 78 to be supplied to an output tip 84. When the user control 82 is placed in the second position, water is supplied from the water line 80 to the output tip 84. Either the air from the air line 78, the water from the water line 80, or both, may be selectively conditioned by a fluid conditioning unit, for example, the fluid conditioning, unit 121 of FIG. 3, according to the configuration of the controller 125 (FIG. 3), for example. In modified embodiments, the fluid conditioning unit 121 may be provided in a form of a cartridge or cartridges that can be coupled to one or more of an existing air line, water line, or air/water line, to thereby provide fluid conditioning thereto, wherein the cartridge or cartridges can be coupled at any point on the air and/or water line from a source end where the air and/or water is provided into a room to where the air and/or water is output onto an operation site.

Figure 7:
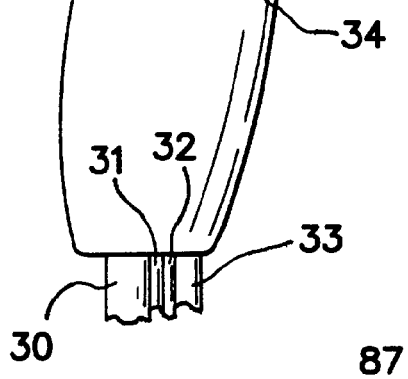
Figure 7:
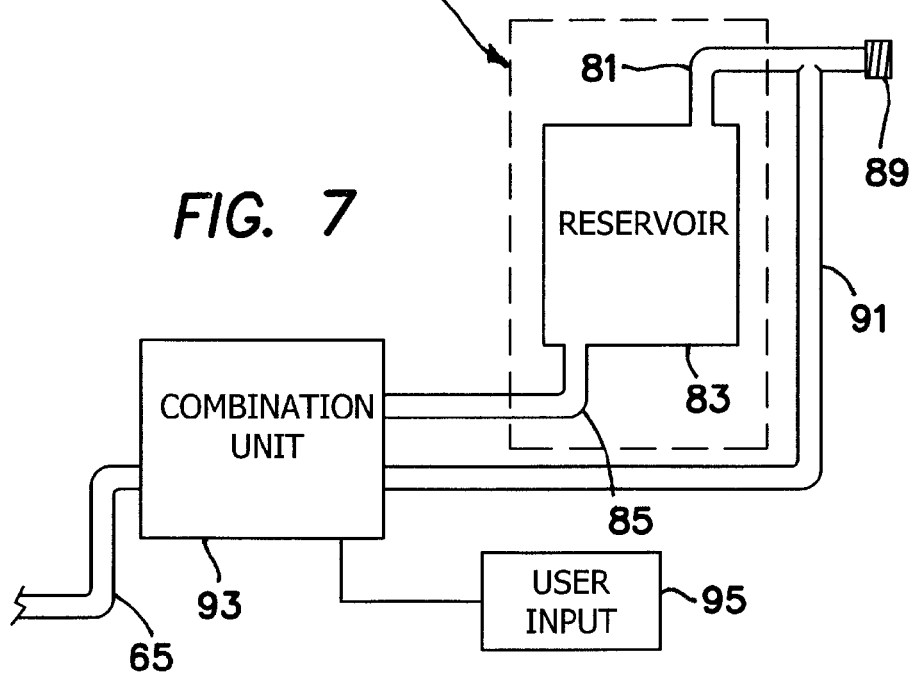

Turning to FIG. 7, a portion of an embodiment of the fluid conditioning unit 121 (FIG. 3), which may be provided, for example, in the form of a removable cartridge, is shown. The illustrated embodiment of the fluid conditioning unit 121 can be adaptable to an existing fluid line or lines (e.g., air, water and/or air/water lines), such as an existing water line 114 (FIG. 3), for providing conditioned fluid to the dental/medical unit 116 as a substitute for regular tap water in drilling and cutting operations, for example. An interface 89 may connect to an existing fluid line, such as an existing water line 114, and may feed fluid (e.g., water) through a fluid-in line 81 and a bypass line 91. The fluid conditioning unit 121 may include a reservoir 83 that accepts water from the fluid-in line 81 and outputs conditioned fluid to a fluid-out line 85. The fluid-in line 81, the reservoir 83, and the fluid-out line 85 together comprise a fluid conditioning subunit 87 in the form of, for example, a cartridge that can be connected to an existing line or lines.

In an illustrated embodiment as shown in FIG. 7, conditioned fluid is output from the fluid conditioning subunit 87 into a combination unit 93. The fluid may be conditioned by conventional means, such as addition of a tablet, liquid syrup, or a flavor cartridge. Also input into the combination unit 93 is regular water from the bypass line 91. Conditioned fluid may exit the combination unit 93 through a fluid tube 65. A user input 95 into the controller 125 (FIG. 3), for example, determines whether fluid output from the combination unit 93 into the fluid tube 65 comprises only conditioned fluid from the fluid-out line 85, only regular water from the bypass line 91, or a combination thereof. The user input 95 may comprise, as examples, a push button, a touch screen, a rotatable knob, a pedal, or a foot switch, or the like, operable by a user, for determining proportions and amounts of conditioned and/or non-conditioned fluid (e.g., water). These proportions may be determined according to a position of the pedal or knob position or ranges programmed on the screen, for example. In the embodiment comprising a pedal, for example, a full-down pedal position may correspond to only conditioned fluid from the fluid-out line 85 being output into the fluid tube 65, and a full pedal up position may correspond to only water from the bypass line 91 being output into the fluid tube 65. In another configuration, the switching between modes and amount of fluid conditioned or non-conditioned delivered to the site can be accomplished through controls on the touch screen (e.g., push buttons or touch buttons). In yet another configuration, mode switching and selection of a fluid type may be voice activated. One or more of the bypass line 91, the combination unit 93, and the user input 95 may provide versatility, but may be omitted, according to preference. A simple embodiment for conditioning fluid comprises only the fluid conditioning subunit 87. Thus, in certain implementations of any of the embodiments described herein, one or more of the bypass line 91 and the combination unit 93 may be omitted. For example, a cartridge may be coupled to an existing line to inject conditioning agents into the existing line, wherein the cartridge does not include a bypass line 91 or a combination unit 93.

Figure 8:
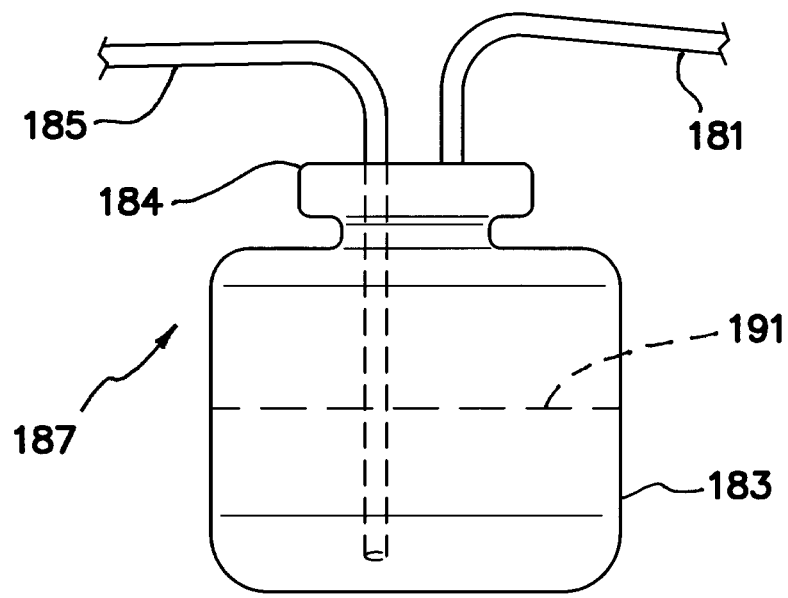
FIG. 8 illustrates one embodiment of a fluid conditioning unit according to the present invention.

An alternative embodiment of the fluid conditioning subunit 87 (FIG. 7) is shown in FIG. 8 identified by reference designator 187. The fluid conditioning subunit 187 may input air from an air line 113 (FIG. 3), which may connect to an air input line 181. Conditioned fluid may be provided via a fluid output line 185. The fluid output line 185 can extend vertically down into a reservoir 183 and into a fluid 191 located therein. A lid 184 of the reservoir 183 may be removed, and conditioned fluid may be inserted into the reservoir 183. Alternatively, a conditioning substance such as anticaries, antiplaque, antigingivitis, and antitartar agents, in a form of a solid (e.g., a tablet or capsule) or liquid form of fluid conditioner may be added to water already in the reservoir 183. In any case, the solid may release the conditioning substance either slowly or quickly into the fluid depending on the application. In one embodiment the solid is an effervescent tablet which can dissolve and mix with fluid at the same time. The fluid can also be conditioned, using a scent, a flavor, an antiseptic, an antibacterial, a disinfectant, or a medication. The medication may take a form of a fluid drop or a tablet (not shown). The fluid 191 further may be supplied with fungible cartridges, for example. The entire reservoir 183 may be disposable or replaceable to accommodate the aforementioned fluid conditioners or different disinfectants, antiseptics, antibacterials, vitamins, flavors or medications.

Figure 9:
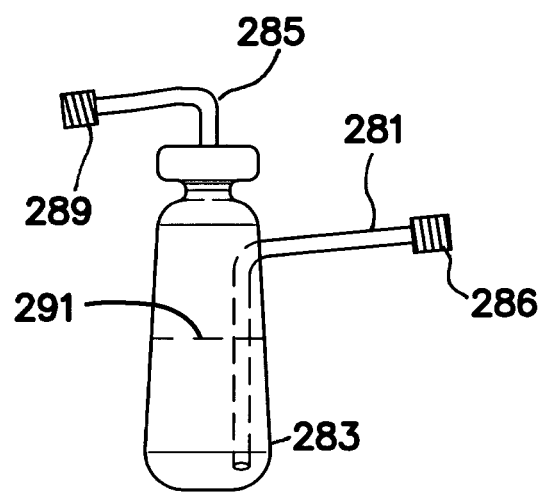
FIG. 9 illustrates an air conditioning unit according to an embodiment of the present invention.

The fluid 191 within the reservoir 183 may be conditioned to achieve a desired flavor, such as a fruit flavor or a mint flavor, or may be conditioned to achieve a desired scent, such as an air freshening smell. In one embodiment wherein the fluid 191 in the reservoir 183 is conditioned to achieve a desired flavor, a flavoring agent for achieving the desired flavor does not consist solely of a combination of saline and water and does not consist solely of a combination of detergent and water. Conditioning the fluid 191 to create ascent, a scented mist, or a scented source of air, may be particularly advantageous for implementation in connection with an air conditioning unit, as shown in FIG. 9 and as described below. In addition to flavor and scents, other conditioning agents may be selectively added through a conventional water line, mist line, or air line, for example, air line 113 and/or water line 114 as illustrated in FIG. 3. For example, an ionized solution, such as saline water, or a pigmented or particulate solution (containing for example bio-ceramics, bio-glass, medical grade polymers, pyrolitic carbon, encapsulated water based gels, particles or water based gel particles encapsulated into microspheres or microparticles) may be added. Additionally, agents may be added to change a density, specific gravity, pH, temperature, or viscosity of water and/or air supplied to a drilling or cutting operation. These agents may include a tooth-whitening agent for whitening a tooth of a patient. The tooth-whitening agent may comprise, for example, a peroxide, such as hydrogen peroxide, urea peroxide, carbamide peroxide or any other agents known to whiten. The tooth-whitening agent may have a viscosity on an order of about 1 to 15 centipoises (cps). Medications, such as antibiotics, steroids, anesthetics, anti-inflammatories, disinfectants, adrenaline, epinephrine, or astringents may be added to the water and/or air used in a therapeutic, drilling, or cutting operation. In one embodiment the medication does not consist solely of a combination of saline and water and does not consist solely of a combination of detergent and water. For example, an astringent may be applied to a surgical area via the water line 114 (FIG. 3) to reduce bleeding. Vitamins, herbs, or minerals may also be used for conditioning air or water used before, during (continuously or intermittently), or after a therapeutic, cutting or drilling procedure. An anesthetic or anti-inflammatory introduced into a conditioned fluid and applied to a surgical wound may reduce discomfort to a patient or trauma to the wound, and application of an antibiotic or disinfectant before, during (continuously or intermittently) or after a procedure may prevent infection to the wound.

An air conditioning subunit connectable into an existing air line 113 (FIG. 3) via interfaces 286 and 289 is illustrated in FIG. 9. The air conditioning subunit may comprise an air input line 281, a reservoir 283, and an air output line 285. Conventional air from, for example, air line 113 enters the air conditioning subunit via the air input line 281, which may be connected to the air line 113, and exits through the air output line 285. The air input line 281 can extend vertically into the reservoir 283 and into a fluid 291 within the reservoir 283. The fluid 291 can be conditioned, using either a scent fluid drop or a scent tablet (not shown). The fluid 291 may be conditioned with other agents, as discussed above in the context of conditioning water. According to the present invention, water in the water line 31 or air in the air line 32 of a conventional laser cutting system (FIG. 2) may also be conditioned. Either or both of the fluid tube 65 and the air tube 63 (FIG. 5a) of an electromagnetically induced disruptive cutter may be conditioned as well. In addition to laser operations, air and/or water of a dental cleaning, whitening, irrigating, suction, electrocautery, or sonic/ultrasonic system may also be conditioned.

Many of the above-discussed conditioning agents may change absorptions of electromagnetic energy by atomized fluid particles electromagnetically induced disruptive (e.g., mechanical) cutting environments as described herein. Accordingly, a type of conditioning may affect the cutting power of an electromagnetic or an electromagnetically induced disruptive cutter. Thus, in addition to direct benefits achievable by incorporation of various conditioning agents discussed above, such as flavor, disinfectants, antiseptics, medication, etc., these various conditioning agents further provide versatility and programmability to the type of cut resulting from use of the electromagnetic or electromagnetically induced disruptive cutter. For example, introduction of a saline solution may change the speed of cutting. Such a biocompatible solution may be used for delicate cutting operations or, alternatively, may be used with a variable laser power setting to approximate or exceed the cutting power achievable with regular water.

Pigmented and/or particulate fluids may also be used with the electromagnetic or the electromagnetically induced disruptive cutter according to the present invention. An electromagnetic energy source may be set for maximum absorption of atomized fluid particles having a certain pigmentation, for example. These pigmented atomized fluid particles may then be used to achieve disruptive cutting. A second water or mist source may be used in a cutting operation. When water or mist from this second water or mist source is not pigmented, the interaction with the electromagnetic energy source may be minimized. As just one example of many, water or mist produced by the secondary mist or water source could be flavored.

According to another configuration, the atomized fluid particles may be unpigmented and/or nonparticulate, and an energy source for the electromagnetic or the electromagnetically induced disruptive cutter may be set to provide maximum energy absorption for these unpigmented atomized fluid particles. A secondary pigmented fluid or mist may then be introduced into the surgical area, and this secondary mist or water would not interact significantly with electromagnetic energy emitted by the electromagnetic or the electromagnetically induced disruptive cutter. As another example, a single source of atomized fluid particles may be switchable between pigmentation and non-pigmentation, and an electromagnetic energy source may be set to be absorbed by one of the two pigment states pigmented and unpigmented) to thereby provide a dimension of controllability as to exactly when cutting is achieved.

In another embodiment, a source of atomized fluid particles may comprise a tooth whitening agent that is adapted to whiten a tooth of a patient as described above. The source of atomized fluid particles may be switchable by a switching device (e.g., by the controller 125 of FIG. 3) between a first configuration, wherein the atomized fluid particles comprise the tooth-whitening agent and a second configuration wherein the atomized fluid particles do not comprise the tooth-whitening agent. In this embodiment, the electromagnetic or electromagnetically induced energy source may comprise, for example, a laser device that is operable between an on condition and an off condition, independently of the configuration of the switching device. Thus, regardless of whether the switching device is in the first configuration or the second configuration, the laser can be operated in either the on or off condition.

Disinfectant (e.g., antibacterial, antiseptic and other such agents) may be added to an air or fluid (e.g., water) source in order, for example, to combat bacteria growth within air and/or water lines (e.g., air line 113 and water line 114 illustrated in FIG. 3) and to minimize bacteria at a tissue site before, during and/or after treatment. The disinfectant, further, may minimize bacteria growth on surfaces adjacent to a location where a procedure is performed. Disinfectant may be applied either continuously or intermittently. As used herein, the term "disinfectant" is intended to encompass various modified embodiments of the present invention, including those embodiments using disinfectants having one or more of chlorine dioxide, stable chlorine dioxide, sodium chlorite, peroxide, hydrogen peroxide, alkaline peroxides, iodine, providone iodine, peracetic acid, acetic acid, chlorite, sodium hypochlorite, hypochlorous acid, sodium chlorate, sodium percarbonate, citric acid, chlorohexidine gluconate, nitrate, silver ions, copper ions, zinc ions, equivalents thereof, and combinations thereof, including those that may or may not include biocompatible base or carrier mediums (e.g., water and other forms of water-based products for surgical procedures).

A disinfectant may be introduced continuously or intermittently, for example, into air, mist, or water used for a dental or medical (e.g., surgical) procedure or application. For instance, in a context of a fluid (e.g., water) line, the disinfectant may be introduced to reduce one or more of a biofilm content within the fluid line and/or a bacterial count of a fluid supplied by the line. This disinfectant can be periodically routed through air, mist, or water lines to disinfect interior surfaces thereof.

With reference to FIG. 3, for example, the air line 113 and water line 114 of the dental/medical unit 116, for example, may be periodically flushed with a disinfectant. In one embodiment, the disinfectant may be selected by the controller 125 and supplied by the fluid conditioning unit 121. In the illustrated embodiment, an optional accessory tube disinfecting unit 123 may accommodate disinfecting cartridges and may perform standardized or preprogrammed periodic flushing operations.

A canister or cartridge (e.g., dispensing housing) may be placed to directly access and teed components disinfectants and/or medicaments) into, for example, a fluid-conditioning air and/or water reservoir (c.f., 281 of FIG. 9 or 185 of FIG. 8) or to directly access and feed components into fluid supply lines such as one or more of an existing air (c.f., 113 of FIG. 3), water (c.f., 114 of FIG. 3), or air/water line, wherein the canister or cartridge may be disposed at any point (e.g., from a supply-line source to a handpiece output) along one or more fluid supply lines of, for example, a conventional, non-conditioning medical or dental system). The canister or cartridge in one embodiment may be placed, for example, downstream of a reservoir, or reservoir location in embodiments without a reservoir, to feed components to for example a handpiece output either continuously or intermittently. In exemplary implementations, the downstream placement may include positioning a replaceable canister within the handpiece or securing the canister to an external surface of the handpiece, so that when the handpiece emits fluid the canister may add a conditioning effect. If, for example, an optional upstream reservoir is also used the downstream placement may add a further conditioning effect to the fluid. According to an implementation wherein the canister or cartridge is disposed adjacent to or within, for example, a laser handpiece, removal of the handpiece from a trunk fiber assembly can provide access to the canister or cartridge for maintenance or replacement. Any conditioning agent, such as, for example, medications, disinfectants (antibacterial and antiseptic agents), flavors, remedies, or vitamins may be applied to a tissue site from, for example, a cartridge or cassette disposed within a handpiece or endoscope according to assorted embodiments of the present invention. In certain embodiments, the cartridge or cassette may be located adjacent to the handpiece or endoscope. Each of these embodiments may allow a correct dose of a fluid conditioning agent (solid or liquid) to be applied to an air or water line or applied through an optional bypass line (e.g., bypass line 91 (FIG. 7)) and thereby to be delivered to a tissue/treatment site. Such a conditioning agent may also be applied as part of a sterile water system connected to a surgical/treatment handpiece or endoscope.

Positions of the canister or cartridge and reservoir may be swapped, or positions of the canister or cartridge and reservoir may be made substantially the same, relative to an upstream or downstream location. As a non-inclusive list of examples, with reference to FIGS. 5a, 5b, 7, 8 and 9, a canister or canisters may be placed in, on, or in proximity to, one or more of an air tube 63 (FIGS. 5a, 5b), fluid tube 65 (FIGS. 5a, 5b, 7), fluid-in line 81 (FIG. 7), reservoir 83 (FIG. 7), fluid-out line 85 (FIG. 7), bypass line 91 (FIG. 7), combination unit 93 (FIG. 7), air input line 181 (FIG. 8), reservoir 183 (FIG. 8), fluid output line 185 (FIG. 8), air input line 281 (FIG. 9), reservoir 283 (FIG. 9), and air output line 285 (FIG. 9).

In modified embodiments implementing a reservoir, the position of the canister or cartridge and reservoir can be made substantially the same, and the canister or cartridge and reservoir may be combined. For example, the canister may be removably placed outside, or within, the reservoir. In an implementation where the canister is placed within a reservoir, which may contain a liquid (e.g., water), the canister can serve to time release predetermined amounts of, for example, silver ions, vitamins, remedies, disinfectants, antiseptics, flavors or medications into the liquid within the reservoir. The canister or cartridge may be disposed within the reservoir by, for example, attachment to an internal surface of the reservoir, and/or attachment to or around one or more elements positioned within the reservoir. For instance, in the embodiments of FIGS. 8 and 9 the canister or cartridge may be disposed around or in-line with either the fluid output line 185 (FIG. 8) or air input line 281 (FIG. 9).

According to one embodiment, the canister or cartridge is positioned and configured to release medicaments and/or disinfectant ions (to be embedded at predetermined concentrations) over a predetermined period of time either continuously, intermittently, or both. As one embodiment, a supply source (e.g., canister) may be configured to feed disinfectant substances such as ions (e.g., silver ions) and/or vitamins, remedies and/or medications into a fluid (e.g., air supply line continuously or intermittently, for example, to supply a certain dose of ions and/or medication for a given procedure or period of use.

In embodiments wherein multiple fluid outputs are used, one or more of the fluid outputs may be configured in accordance with the present invention to emit, continuously or intermittently, in gas, liquid or solution (spray), a substance or quantity that differs in some respect from that emitted from another fluid output or outputs. According to an implementation comprising two fluid outputs, such as that depicted in FIG. 5b, one of the fluid outputs may be configured to emit a substance (e.g., silver ions) that differs in, for example, concentration from the other fluid output. For example, one fluid output may emit the substance with the other not emitting the substance. According to embodiments incorporating greater numbers of fluid outputs, such as disclosed in U.S. Provisional Patent Application No. 60/538,200, filed Jan. 22, 2004 and entitled ELECTROMAGNETICALLY INDUCED CUTTER AND METHOD, the entire contents of which are incorporated herein by reference, one or more of the fluid outputs (e.g., nozzles) may be configured to emit, continuously or intermittently, in gas, liquid or solution (spray), for example, a substance than has a greater disinfecting, cosmetic and/or medicating property than that emitted from the other fluid output or outputs.

Routing of disinfectant can be performed between patient procedures, daily, or at any other predetermined intervals. For example, in certain instances the disinfectant may be applied before, during (continuously or intermittently) or immediately following patient procedures, wherein concentrations of disinfectant may be varied accordingly In embodiments wherein one or more fluid outputs is/are used, a given one or more of those fluid outputs may be configured in accordance with the present invention to emit, continuously, or intermittently, in gas, liquid and/or solution (e.g., spray), a substance or quantity that differs in some respect from that emitted from (a) another fluid output or outputs and/or (b) the given fluid output or outputs at another point in time. A given fluid output may be configured to emit a substance (e.g., silver ions) that differs in, for example, one or more of quantity, composition, or concentration from an emission of the given fluid output at a prior or subsequent point in time. For example, a given fluid output may be configured to emit, continuously or intermittently, in gas, liquid or solution (spray), a substance than has a greater disinfecting, cosmetic and/or medicating property than that emitted from the given fluid output at a different (e.g., immediately preceding or following) point in time when the given fluid output is emitting the same or the same type (e.g., similar but not identical in one or more properties, or substantially identical) of substance or outputs.

The disinfectant, antiseptic and/or antibacterial may consist of or include one or more of chlorine dioxide, stable chlorine dioxide, sodium chlorite, peroxide, hydrogen peroxide, alkaline peroxides, iodine, providone iodine, peracetic acid, acetic acid, chlorite, sodium hypochlorite, citric acid, chlorohexidine gluconate, disinfectant ions (e.g., silver ions, copper ions and zinc ions), equivalents thereof, and combinations thereof which may or may not include biocompatible base or carrier mediums (e.g., water). Exemplary concentrations (by volume) of the above-listed items may be chosen as listed in Table 1 when used, for example, between procedures.

TABLE 1

| Disinfectant | Lower limit | Upper Limit | Typical |
|---|---|---|---|
| Chlorine dioxide | 0.099% | 0.9% | |
| Stable chorine dioxide | | | |
| Sodium chlorite | | | |
| Hydrogen peroxide | 0.1% | 30% | 4.6% |
| Alkaline peroxides | 0.1% | 30% | 4.6% |
| Providone iodine | 0.1% | 15% | |
| Peracetic acid | 0.05% | 6% | 0.08%, 4.5% |
| Acetic acid | 0.01% | 10% | 6.5% |
| Chlorite | 0.1% | 2% | 0.4%-0.6% |
| Sodium hypochlorite | 0.1% | 5% | |
| Hypochlorous acid | 0.01% | 0.1% | |
| Sodium chlorate | 0.0002% | 0.002% | |
| Bio-compatible alcohol | 0 | 25% | |
| Citric acid | 1% | 75% | |
| Chlorohexidine gluconate | 0.05% | 20% | |
| Silver ions | 0.9 mg | 2 mg | |
| Fluoride ions | 0.15% | 0.5% | |
| Copper ions | * | * | * |
| Zinc ions | * | * | * |

* Use in quantities recommended as acceptable by the Environmental Protection Agency (EPA)

When used, for example, during procedures, item concentrations (by volume) may be chosen as listed in Table 2.

TABLE 2

| Disinfectant | Lower Limit | Upper Limit | Example |
|---|---|---|---|
| Chlorine dioxide | 0.001% | 0.099% | |
| Stable chorine dioxide | | | |
| Sodium chlorite | | | |

TABLE 2-continued

| Disinfectant | Lower Limit | Upper Limit | Example |
|---|---|---|---|
| Hypochlorous acid | 0.0001% | 0.009% | |
| Silver nitrate | 0 | 0.6% | |
| Eucalyptol | 0 | 0.9% | |
| Menthol | 0 | 0.5% | |
| Thymol | 0 | 0.,7% | |
| Bio-compatible alcohol | 0 | 12% | |
| Chlorohexidine gluconate | .05% | 20% | 0.12% |
| Silver ions | 0.0015 mg | 0.9 mg | |
| Fluoride ions | 0.0001% | 0.15% | |
| Sodium fluoride | 0.05% or 225 ppm | 0.2% or 990 ppm | |
| Stannous fluoride | 0.1% or 244 ppm | 0.4% or 1000 ppm | |
| Copper ions | * | * | * |
| Zinc ions | * | * | * |

* Use in quantities recommended as acceptable by the Environmental Protection Agency (EPA)

Regarding the exemplary concentrations set forth above, and in the context of any implementations described herein, wherein for example fluids having different fluid properties (e.g., quantities, compositions, or concentrations) are output by one or more of (a) the same fluid output at different times or (b) different fluid outputs at the same or different times, the different fluid properties may be achieved by way of operation of a controller (e.g., controller 125 of FIG. 3) and/or by operation of a user, for example, switching between one or more fluid-conditioning, canisters or cartridges.

According to a typical implementation, a first fluid conditioning cartridge may be coupled to a fluid (e.g., water) supply line using any means recognizable as suitable by those skilled in the art, to deliver a first conditioning agent, such as a disinfectant at an in-procedure concentration. The concentration provided by the first fluid conditioning cartridge to the fluid supply line may be altered using any means suitable for achieving such an effect, such as by operation of a controller 125 under the influence of a pre-programmed or real-time input. In other implementations, the concentration provided by the first fluid conditioning cartridge to the fluid supply line may be maintained substantially constant for so long as the first fluid conditioning cartridge remains connected to the fluid supply line, which can be only during a procedure or for the duration of a day, week, month, and the like.

A second fluid conditioning cartridge may be coupled to the fluid supply line using any means recognizable as suitable by those skilled in the art, to deliver a second conditioning agent, such as a disinfectant at a between-procedures concentration. For example, in one implementation the first fluid conditioning cartridge for delivering the first conditioning agent may be decoupled from a point on the fluid supply line and the second fluid conditioning cartridge (e.g., having a similar construction and/or connecting structure) may be coupled to the fluid supply line at the same point. In accordance with another implementation, the second fluid conditioning cartridge may be coupled to the first fluid conditioning cartridge or to the fluid supply line while the first fluid conditioning cartridge remains connected thereto. Operation of either one of the first fluid conditioning cartridge and the second fluid conditioning cartridge, or combinations of both, may be selected by operation of a controller, by manual action from a user, by pre-programming, by an input from a user, or by combinations thereof.

The concentration provided by the fluid conditioning cartridge to the fluid supply line may be altered using any means suitable for achieving variances in fluid concentrations, such as by operation of a controller 125 under the influence of a pre-programmed or real-time input. In other implementations, the concentration provided by the fluid conditioning cartridge to the fluid supply line may be maintained substantially constant for so long as the fluid conditioning cartridge remains connected to the fluid supply line, which can be only during a procedure or for the duration of a day, week, month, and the like.

One exemplary implementation may comprise a laser system with a first conditioning cartridge connected to, for example, a fluid (e.g., water) supply line for the deliverance of a first conditioning agent (e.g., an in-procedure concentration of disinfectant) during procedures throughout the day.

According to certain implementations, the first conditioning agent can be delivered throughout the day (e.g., continuously so that all fluid, such as water, that is drawn from the fluid supply line is conditioned) regardless of whether or not a given procedure or type of procedure is being performed. In other implementations, the first conditioning agent is delivered only during procedures or at selected (e.g., predetermined or real-time selected) times under the control of, for example, one or more of a past or present input, such as a user input, whereby, for example, the user can select a non-conditioned fluid (or a different concentration of fluid, or a fluid having one or more different properties) to be delivered at various times. At the end of the day (or at some other time, such as at the end of a procedure or the end of a week) a connected first fluid conditioning cartridge may be decoupled from the fluid supply line with a second conditioning cartridge being connected thereto instead for the deliverance of a second conditioning agent (e.g., a between-procedures concentration of disinfectant) for disinfecting equipment (e.g., the fluid supply line and/or other lines). A manual or automated disinfecting procedure may then be performed. At a subsequent point in time, such as the following morning, the second fluid conditioning cartridge may be replaced with the, or another, first fluid conditioning cartridge for the deliverance of the first conditioning agent. At any point following the disinfecting procedure, such as at any time prior to a procedure, the lines that were disinfected using the second fluid conditioning cartridge may be flushed or purged using, for example, a non-conditioned fluid or a fluid conditioned with the first conditioning agent.

For individuals with high risk for dental caries a higher percentage of sodium fluoride is recommended during procedures. For example, about 1.1% acidulated NaF (5000 ppm) or 1.1% neutral Naf (5000 ppm) can be used in certain embodiments. One or more of the concentrations listed in Tables 1 and 2 may be effective in certain embodiments for facilitating one or more of biofilm removal and viable count reduction of bacteria. In another embodiment an amount of stable chlorine dioxide or sodium chlorite during patient treatment may be between 5 ppm to 150 ppm. Between procedures as a purge the amount may be between 50 ppm to 1,200 ppm. Other ranges may include between 100 ppm to 150 ppm or more specifically between 10 ppm to 300 ppm. Chlorine dioxide may be released from a two component system. In this case a first component may be sodium chlorite, for example, and a second component may be an acid such as citric acid, ascorbic acid vitamin C), phosphoric acid, carbonic acid, and lactic acid, as well as others.

The disinfectant (e.g., antibacterial or antiseptic agents) described herein may be applied, either intermittently or continuously, during, or at or near completion of a medical or dental procedure. Air and water used to cool and assist with tissue cutting or drilling within a mouth of a patient or at any other surgical site, for example, is often vaporized into the surrounding air to some degree. The air and water also may be projected onto a tissue target surface or onto adjacent instrumentation. According to the present invention, a conditioned disinfectant solution may also be vaporized with the air or water, and may condense onto surfaces of the tissue target or onto adjacent dental/medical instruments and equipment within a dental/surgical operating room. Any bacteria growth on these moist surfaces may thus be significantly attenuated as a result of a presence of the disinfectant on the surfaces. In accordance with another aspect, disinfectant (e.g., antibacterial or antiseptic agents), such as a liquid or solid dissolvable in liquid, may be applied (e.g., sprayed), for example, during procedures (continuously or intermittently) to decontaminate (e.g., provide an anti-microbial effect on or within) an area of interest (e.g., a patient's mouth or surgical site) and/or clean the air and/or water tubes. The disinfectant may comprise one or more of for example, chlorine dioxide or stable chlorine dioxide (sodium chlorite plus acid) or any other disinfectants, antibacterial or antiseptic agents listed above or in combination with ions, such as silver, fluoride, copper, or zinc ions, equivalents thereof, and combinations thereof including biocompatible base or carrier mediums (e.g., water and other surgical fluids). Other combinations my comprise a disinfectant (e.g., antibacterial or antiseptic agents) or medicament or flavor with one or more of the following substances: vitamin C (ascorbic acid), vitamin E, vitamin $B_1$ (thiamin), $B_2$ (riboflavin), $B_3$ (niacin), $B_5$ (pantothenic acid), $B_6$ (pyridoxal, pyridoxamine, pyridoxine), $B_{12}$ (cobalamine), biotin or B complex, bioflavonoids, folic acid, vitamin A, vitamin D, vitamin K, aloe vera, a natural anti-inflammatory, antioxidant or anti histamine remedy, and other such ingredients and solutions. In other embodiments, the disinfectant may comprise, for example, ions, such as silver, copper, or zinc ions, equivalents thereof, and combinations thereof, which may or may not include bio-compatible base or carrier mediums (e.g., water).

While, according to certain aspects of the present invention, the above-listed items can be used individually, other aspects of the present invention can comprise combinations of one or more of the above-listed items with or without disinfectant ions. Other embodiments may comprise combinations of two or more of the above-listed items, wherein such combinations may be formed with or without disinfectant ions. Concentrations of the above-listed items may be chosen as follows:

Chlorine dioxide (e.g., sodium chlorite plus acid), which may be desired as a disinfectant for its affordability and efficacy, may be used during the aforementioned procedures at adequate concentrations without adverse side effects. That is, chlorine dioxide is relatively nontoxic at low concentrations and so can be used during procedures as well as, for example, for purging lines between procedures. The chlorine dioxide can be combined with, for example, silver ions (see acceptable range above).

A hydrogen peroxide based solution for disinfecting may be used alone or in combination with other disinfectants. For example, hydrogen peroxide may be used in combination with peracetic acid (in concentrations ranging from about 0.05% to about 4%, e.g., 0.8% by volume when used between procedures) or acetic acid (in concentrations from about 0.01% to about 10% by volume when used between procedures) or in combination with silver ions (see acceptable range above).

Sodium hypochlorite can be combined with, for example, citric acid (1% to 75% volume when used between procedures) and/or with disinfectant ions.

According to another feature of the present invention, when disinfectant is routed in fluid through lines during a medical procedure, the disinfectant stays with the fluid (e.g., water) or mist, as the water or mist becomes airborne and settles (i.e., condenses) on surrounding surfaces within the dental operating room. Bacteria growth within the lines, and from the condensation, is significantly attenuated, because the disinfectant kills, stops and/or retards bacteria growth inside the fluid (e.g., water) lines and/or on any moist surfaces.

The introduction of disinfectant, antibacterial or antiseptic ions, may be carried out for purposes including:

1) Disinfection of fluid lines, thereby reducing biofilm and/or keeping bacterial count low;

2) Decontamination (e.g. causing ions to act as an antimicrobial agents) of a tissue target that is being worked on (e.g., cut, ablated, or decontaminated) with, for example, a laser device prior to, during (continuously or intermittently) and/or at completion of a medical procedure, such as, (or example, irrigation with fluids (gas or liquid) during a laser procedure;

3) Projection of disinfectant ions onto a surface of targeted tissue (hard or soft) thereby temporarily or permanently embedding the ions into the surface or deeper into tissue in order to decontaminate or treat the tissue. For example, ions such as fluorine ions may act tong term as an anti-microbial agent or may perform other functions, such as caries prevention;

4) Application at completion of a surgical procedure as an anti-microbial agent before a wound is closed or covered with a restorative material; and 5) To project and cover material (e.g., hard or soft tissue) or to embed into material (e.g., hard or soft) compounds, ions or particles to coat or attach to such material (e.g., hard or soft tissue) through surface tension, adhesion, micromechanical retention and the like. Embedding may include simultaneously remodeling of hard or soft tissue as disclosed in U.S. application Ser. No. 11/033,032, filed Jan. 10, 2005 and entitled ELECTROMAGNETIC ENERGY DISTRIBUTIONS FOR ELECTROMAGNETICALLY INDUCED DISRUPTIVE CUTTING, wherein benefits such as caries prevention and the like along with ion benefits may be obtained, Other products used to decontaminate may include other types of ions such as Al, Ca, Ce, Mg, Sr, Sn or Ti. Such products are described in, for example, U.S. Pat. No. 6,827,766 (e.g., see, for example, the abstract and Col. 2,122 to col. 3,162), the entire contents of which are expressly incorporated herein by reference. Stilt further, silver ions may be incorporated into water or another type of fluid, or a colloidal solution (e.g., colloidal silver aggregate) that contains silver particles may be used. Copper or zinc may or may not be used in place of silver in these instances. Silver particles (e.g., ions) can be about 20 Å, 10 Å, or less in diameter (e.g., about 8 Å in one embodiment). In another formulation, a colloidal silver aggregate can have zeta potential (i.e., can be formed as colloidal silver having a higher charge density (or concentration) than is normally obtained with a similar number of single silver ions dispersed through a fluid). This type of colloidal silver aggregate has been used for wound dressings or wound care. Silver can provide extremely small particle sizes for permeating cell (e.g., pathogen) membranes in order to accomplish a variety of antimicrobial actions (e.g., actions disabling a pathogen from reproducing).

With regard to the use of colloidal silver aggregate as a disinfectant, EPA recommendations should be followed where applicable. EPA studies have shown that an amount of silver intake in order to be at risk for argyria (a permanent dark discoloration of skin caused by over use of medicinal silver preparations) is 3.8 to 6 grams of silver. According to another EPA guideline, a critical daily dose of silver for a 160 pound adult is 1.09 mg. This dosage is below the critical daily intake for the development of argyria as recommended by the EPA. One teaspoon of 5 ppm colloidal silver contains about 25 micrograms of silver, or 0.025 milligrams of silver. Six teaspoons, the equivalent of one fluid ounce, therefore contains 0.15 milligrams of silver.

The FDA has approved antibacterial silver for food industry applications. An article appearing at http://www.silver-medicine.org/ag-ions-1.html reported that, AgIONS Technologies incorporated received approval by the FDA in October 2003 for use of antibacterial silver in the food industry. The FDA informed AgIONS Technologies that the product had been added to the FDA's list of food contact substances. The AgIONS Type AK product was comprised of 5% silver contained within an inert crystalline carrier. When subject to small amounts of moisture, AgIONS begin to release silver ions, which then act to eliminate bacterial growth on treated surfaces. AgIONS was specifically designed and engineered as a surface treatment system, with wide applications in the food processing industry. Since most food processing plants have a zero tolerance policy for bacterial spoilage, the use of silver to treat surfaces and equipment used in food processing was expected to greatly reduce bacterial growth.

One embodiment of the present invention uses only non-toxic silver salts combined with fluid (e.g., water) as part of a fluid conditioning process as described herein.

Silver or other ions (e.g., copper, zinc, fluoride, etc.) may be combined with other disinfectants (e.g., chlorine dioxide, peroxides, and/or other medical/dental disinfectants, such as hypochloric acid), for disinfecting water lines. For antiseptic applications (i.e. for application to tissue), silver ions may be combined with antiseptics. The silver ions may operate to have combined action with radical oxygen toxic species (ROTS), examples of which may include peroxides (e.g., hydrogen peroxide). ROTS also may be combined with antioxidants (e.g., selenium or vitamin E) in some medical/dental applications.

U.S. Pat. No. 4,915,955 discloses a product used to disinfect dental (e.g., water and/or air) lines (e.g., purge water and/or air lines one time), which may comprise, for example, hydrogen peroxide (5%) and silver ions. A reprint from http://silverdata.20m.com/h2o2.html reports that "[a]ccording to Water and Science Technology, Volume 31 5-6, a 1000:1, solution of colloidal silver to hydrogen peroxide is sufficient to increase the efficacy of colloidal silver by up to 100 times under some circumstances (which may remain unknown) against bacterial infections"

Water, including ingredients that may be preservatives (or have at least partial preservative properties) that imbue the water with bacteriostatic properties, may be employed in some embodiments.

Chemicals that may be incorporated into water in order to prevent growth of microorganisms (i.e., to introduce bacteriostatic properties into the water) include:
1) Sodium chloride (NaCl);
2) Sugars such as sucrose, dextrose, and fructose;
3) Organic acids such as acetic acid (vinegar), lactic acid, citric acid, propionic acid, ascorbic acid, benzoic acid (also called benzoates);
4) Nitrates and nitrites; and
5) Oxides such as sulfur dioxide, ethylene oxide, and propylene oxide.

According to an embodiment, fluid containing ions may be sprayed before, during continuously or intermittently), and/ or after tissue cutting, wherein, for example, the concentrations may differ at different times (e.g., those of Table 1 being, applied during a procedure and those of Table 2 being applied before or after the procedure). In other embodiments, the fluid may be sprayed at completion of a procedure after tissue is cut. Spray may be delivered during (continuously or intermittently) or after cutting and/or may be delivered before covering tooth, bone or other tissue with for example a protectant. Biocompatible amounts may be applied, for example, using ion concentrations similar to those used for employing ions to protect wounds in the prior art. In hard tissue when a cut is covered, although ions may stay entrapped, their effect normally will be harmless.

The information provided herein may be applied to treatment of both hard and soft tissues. Recipes for obtaining colloidal suspensions of silver and other ions in aqueous solution are available in the prior art. For example, recipes for compounds that include antibacterial cations such as silver, zinc, copper, etc. are described in U.S. Pat. No. 6,759,544, which recipes are included herein by reference.

U.S. Pat. No. 6,827,766, the entire contents of which are expressly incorporated herein by reference, includes a description on formulation of nanoparticle biocides in forms of sprays, fogs, aerosols, and the like.

U.S. Pat. No. 6,051,254, the entire contents of which are expressly incorporated herein by reference, discloses a pharmaceutical formulation comprising an amoxycillin hydrate that may, when made up in an aqueous solution, be applied according to an implementation of a method of the present invention.

Another aspect of the present invention may comprise a method of delivering ions (e.g., disinfectant and/or other ions) to a target surface, details of which are disclosed U.S. application Ser. No. 11/033,032, filed Jan. 10, 2005 and entitled ELECTROMAGNETIC ENERGY DISTRIBUTIONS FOR ELECTROMAGNETICALLY INDUCED DISRUPTIVE CUTTING. Particles, which may comprise selected types of ions (e.g., silver, copper, zinc, fluoride or other ions), may be projected onto the target surface. According to an exemplary embodiment, an air spray, fluid spray or a combination spray of both air and fluid (e.g., water) may be used to project particles (e.g., disinfectant ions, other ions, and/or ionic compounds) onto the target surface before, during (continuously or intermittently) or after a procedure in order to allow the particles to attach or adhere (e.g., to micromechanically bond) to the surface. For instance, particles (e.g., disinfectant ions) may be fed into a gas line (e.g., an air line of a handpiece) and delivered to a target surface under pressure of air (with or without simultaneous application of liquid) to thereby project particles onto and/or into the target surface. According to one implementation, the surface may or may not be remodeled as described, for example, in the above-incorporated application, wherein the remodeled tissue layer may be more resistant to caries formation. The process further may stimulate formation of secondary dentin and/or may cause the surface to exhibit antibacterial properties. According to another aspect of the present invention, a lamination layer may be applied over a target tissue surface so that the tissue surface is laminated with various ionic compounds and then remodeled with a laser. In a modified implementation, the tissue may be laminated and remodeled at the same time. Either a wet or dry environment may be employed to implement ions into the tissue.

As examples, ions from a list including silver, copper, zinc, fluoride, calcium, phosphorous, hydroxide, combinations thereof, and ionic compounds including one or more of the preceding, may be selected that may, for example, enhance caries prevention. As another example, compounds containing ions, such as sodium fluoride, stannous fluoride, copper fluoride, titanium tetrafluoride, amine fluorides, calcium hydroxide, silver compounds, copper compounds, zinc compounds, combinations thereof, and the like, may be selected. It should be noted that some of these compounds may be compatible with soft tissue, and some may be compatible with dentin, enamel, or bone only. More particularly, compounds having, for example, a fluoride ion may be effective as anti-caries and desensitizing agents. In accordance with one example, fluoride may act to desensitize dental tissue to effects of, for example, heat and cold. In modified embodiments, compounds including, for example, calcium may aid in forming an anti-bacterial surface. In still further embodiments, remineralization of affected dentin may be enhanced by employing, for example, calcium hydroxide or zinc oxide. These compounds may be delivered, for example, through water or other biocompatible fluids that may, for example, contain salt, are sterile, and/or are low in bacterial count.

The ionic compounds may be applied simultaneously (continuously or intermittently) with application of a laser beam, thereby achieving placement of ions and, at the same time, optionally remodeling surface tissue and impregnating ions into a remodeled layer of tissue. Alternately, an area to be treated first may be sprayed continuously or intermittently with one or more ion-containing compounds, such as a topical fluoride preparation, followed by subsequent application of laser energy.

With reference to FIGS. 22-25, additional disclosure is provided in the form of a fluid conditioning system configured as a fluid supply and/or fluid control arrangement or assembly. The assembly may be adapted in whole or in part to existing medical and dental apparatuses, including those used for cutting, irrigating, evacuating, cleaning, drilling, and/or therapeutic procedures. According to one feature, the fluid conditioning system may be embodied, for example, as a fluid controller to employ conditioned (e.g., sterile) fluid in place of or in addition to regular tap water or other types of liquid (e.g., distilled water, deionized water, or water with a controlled number of colony forming units (CFU) per milliliter, and the like), during various clinical operations.

A fluid controller for use in an exemplary context of an electromagnetic-energy assisted operation or procedure (e.g., surgery) can be embodied with a fluid controller (e.g., comprising a flow-control cassette) for directing fluid (e.g., conditioned fluid) toward a target (e.g., tissue) whereby electromagnetic (e.g., laser) energy can be focused in the same direction to disrupt (e.g., ablate or cut) or treat the target, with the fluid controller operating to direct the conditioned fluid in the same direction to effectuate the disrupting or treating. The fluid may be supplied as and/or conditioned fluid comprising or being, for example, a sterile fluid. In certain embodiments, the fluid may be supplied and/or conditioned to comprise or be, for example, a liquid such as water, while in other embodiments it may comprise or be, for example, sterile water. For instance, fluid-controller assemblages may be constructed to controllably provide fluid such as conditioned fluid (e.g., sterile water).

FIG. 22a depicts a fluid controller in the form of a sterile water controller adapted for use with an existing Waterlase MD system 31 or Waterlase MBA system according to an embodiment of the present invention, and FIG. 22b diagrams a fluid controller exemplified as a sterile water kit suitable for use in particular with an existing Waterlase MD system 31 according to an embodiment of the present invention. A fluid controller 30 (also referenced herein as a water control or a cassette controller), supported for instance by a pole on wheels, is operatively coupled via a water connector 32 to a water bottle 33, which may comprise, for example, a source of clean water 33a or a sterile solution bag 33.

The fluid controller 30 is further and/or alternatively operatively coupled to (and/or comprises, or is) a flow-control cassette 35, which typically is positioned downstream of the water bottle 33 and/or operatively coupled via a handpiece connector 37 to a handpiece 39 (e.g., a sterile handpiece). A water line 40 can be connected to supply fluid (e.g., water) from the flow-control cassette 35 to the handpiece connector 37. Additionally and/or alternatively, an air connector 42 (also referenced herein as an air intake) can couple a source of air (not shown) to an air-flow controller 44, which may comprise, for example, a fixed air regulator 44a (e.g., 30 PSI) and/or an air flow control module 44b (e.g., proportional valve). The air-flow controller 44 may be coupled to an air filter 45, which can be coupled to an air line 46 which in turn can be coupled to the handpiece connector 37. Fiber cable attachments 47 can be used to hold the water line 40 and the air line 46. The assemblage of elements between the water connector 32, air connector 42, and handpiece connector 37 of either of FIGS. 22a and 22b may be referred to and used as a disposable sterile set assembly or disposable tubing assembly 48.

A fluid controller according to a typical incarnation can comprise a water-spray upgrade kit, adaptable for use with an apparatus comprising an electromagnetic energy source and a fluid output such as described above or a Waterlase MD laser system 31. The electromagnetic energy source can house, for example, an air control/water control (ACWC) control board 31a, an ACWC manifold 31b, and cassette controller lines 31c, the latter of which may in one implementation comprise part of a disposable tubing assembly 48. The fluid controller may be configurable to operate as a sterile water (e.g., a saline solution, or a balanced saline solution) delivery system for the apparatus or Waterlase M D laser system for uses including but not limited to, dental, ophthalmic and surgical procedures.

FIG. 23 is a block diagram of a fluid controller in the form of a sterile water controller 30 according to an exemplary arrangement of the present invention. Here, an air filter 45 is coupled between an air line 46 and an air-flow controller 44. The air-flow controller 44 can couple a source of air 50 to, for example, a fixed air regulator 44a (e.g., 30 PSI) and/or an air flow control module 44b (e.g., proportional valve). Furthermore, an air pressure ON/OFF (3-way valve) 53 can be coupled between the ACWC control board 31a, the water bottle 33, and the air-flow controller 44.

With regard to sterile-water kit embodiments, such as depicted in FIG. 22b for use/installation with/on existing Waterlase MD systems, such can be implemented with, for instance, an MD handpiece that is slightly modified or redesigned to allow for external connection of the air and water lines. The kit can be provided with, for example, a cassette housing (water flow control) with mechanical features to attach externally to a current MD system. The kit can comprise, for instance, five subsystems, each having a separate specification, as follows: sterile spray air control/water control (ACWC), water bottle, disposable sterile assembly, sterile handpiece, and sterile solution bag. The sterile spray ACWC can comprise an ACWC as provided on the current Waterlase MD with additional components of an air selector valve, cassette control valves (3), control PCB, and cassette housing. The water bottle/sterile solution bag holder can comprise a bottle similar to that currently on production with the Waterlase MD system, but with, e.g., a piercing straw feature for the sterile solution bag. Furthermore, the disposable sterile assembly can comprise a water flow control cassette, sterile air fitter, and sterile tubing set for air and water with fittings, whereby the air and water flow can be comparable to existing Waterlase MD flow levels. According to a particular embodiment, flow control (e.g., all flow control) can be set using existing graphic user interface (GUI) controls.

In the embodiment illustrated in FIG. 23, an air regulator 55, a water regulator 56, a DC input 57, a START/STOP input 59, i.e., for receiving start and stop signals from a footswitch, and an ON/OFF button 63 operate together as part of an air control/water control (ACWC) controller board 60 (cf. 31a, FIG. 22b). The schematic diagram in FIG. 24 depicts a sterile water flow-control cassette 35 according to an implementation of the present invention, in which a water connector 32 and a water line 40 operate to input water into and output water from, respectively, the flow-control cassette 35.

Upon entering the flow-control cassette 35, water is influenced and/or enabled to move toward the water line 40 via a selected two or more of a plurality of flow-control passages. As presently embodied, at least two of the flow-control passages have different resistances to flow. For example, the two or more flow-control passages may be provided with different lumen constructions thereby providing them with different resistances to flow. In one implementation, the two or more flow-control passages are provided with different cross-sectional areas. A particular example can comprise each being provided with a flow restrictor 66 and a pinch (e.g., electronically controlled on/off) membrane 68. As presently embodied, provision of each passage with a different resistance to flow conveniently and reliably provides for a relatively large number of different flow-resistances through the flow-control cassette 35. For instance, while the number of flow-control passages can range from four to eight, or alternatively two to three, or even nine to twenty, for instance, the illustrated arrangement utilizes three selectable flow-control passages A, B and C, to provide respective resistances to flow of "1," "2" and "4," and further to provide additional selectable resistances to flow of "3" (AB), "5" (AC), "6" (BC), and "7" (ABC) through the flow-control cassette 35.

The architecture of FIG. 25 provides a schematic diagram of a sterile water flow-control cassette 35 according to another implementation of the present invention. Here, provision of each flow-control passage with a different resistance to flow conveniently and reliably provides for a relatively large number of different flow-resistances through the flow-control cassette 35. As with the implementation of FIG. 24, each flow-control passage can be (a) preset and/or preconfigured to have a predetermined flow rate and (b) during use can be either selected to be all the way "on" (e.g., enabled) or deselected to be all the way "off" (e.g., disabled). In a preferred embodiment, partial selection or partial deselection of any one or more of the flow-control pathways is not possible or is not enabled thereby providing for a low-cost, simple construction, precision, and/or reliable operation.

With more particular reference to FIG. 25, the illustrated arrangement comprises three flow-control passages CH1, CH2 and CH3, each with a respective different flow resistance. For instance, the flow-control passages CH1, CH2 and CH3 can be provided with different cross-sectional shapes, materials, interior surfaces or structures, path lengths, and/or areas. In the illustrated example, the flow-control passages CH1, CH2 and CH3 can be provided with different cross-sectional areas such as defined by the diameters of CH1 (0.003"), CH2 (0.004") and CH3 (0.005"). Under an input pressure of 35 PSI, for instance, the flow-control passages CH1, CH2 and CH3 may provide different flow rates such as CH1 (3 ml/min), CH2 (6 ml/min) and CH3 (10 ml/min) thereby to provide a flow-control cassette 35 controllable to provide flow rates of 3, 6, 9, 10, 13, 16 and 19

According to certain implementations, laser energy from the trunk fiber is output from a power or treatment fiber, and is directed, for example, into fluid (e.g., an air and/or water spray or an atomized distribution of fluid particles from a water connection and/or a spray connection near an output end of a handpiece) that is emitted from a fluid output of a handpiece above a target surface (e.g., one or more of tooth, bone, cartilage and soft tissue). The fluid output may comprise a plurality of fluid outputs, concentrically arranged around a power fiber, as described in, for example, application Ser. No. 11/042,824 and Prov. App. 60/601,415. The power or treatment fiber may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed, for example, in the below-referenced U.S. Pat. No. 5,574,247, which describes the impartation of laser energy into fluid particles to thereby apply disruptive forces to the target surface.

By way of the disclosure herein, a laser assembly has been described that can output electromagnetic radiation useful to diagnose, monitor and/or affect a target surface. In the case of procedures using fiber optic tip radiation, a probe can include one or more power or treatment fibers for transmitting treatment radiation to a target surface for treating (e.g., ablating) a dental structure, such as within a canal. In any of the embodiments described herein, the light for and/or diagnostics may be transmitted simultaneously with, or intermittently with or separate from, transmission of treatment radiation and/or of the fluid from the fluid output or outputs.

Corresponding or related structure and methods described in the following patents assigned to Biolase Technology, Inc, are incorporated herein by reference in their entireties, wherein such incorporation includes corresponding or related structure (and modifications thereof) in the following patents which may be, in whole or in part, (i) operable with, (ii) modified by one skilled in the art to be operable with, and/or (iii) implemented/used with or in combination with, any part(s) of the present invention according to this disclosure, that of the patents or below applications, and the knowledge and judgment of one skilled in the art.

Such patents include, but are not limited to U.S. Pat. No. 7,578,622 entitled Contra-angle rotating handpiece having tactile-feedback tip ferrule; U.S. Pat. No. 7,575,381 entitled Fiber tip detector apparatus and related methods; U.S. Pat. No. 7,563,226 entitled Handpieces having illumination and laser outputs; U.S. Pat. No. 7,467,946 entitled Electromagnetic radiation emitting toothbrush and dentifrice system; U.S. Pat. No. 7,461,982 entitled Contra-angle rotating handpiece having tactile-feedback tip ferrule; U.S. Pat. No. 7,461,658 entitled Methods for treating eye conditions; U.S. Pat. No. 7,458,380 entitled Methods for treating eye conditions; U.S. Pat. No. 7,424,199 entitled Fiber tip fluid output device; U.S. Pat. No. 7,421,186 entitled Modified-output fiber optic tips; U.S. Pat. No. 7,415,050 entitled Electromagnetic energy distributions for electromagnetically induced mechanical cutting; U.S. Pat. No. 7,384,419 entitled Tapered fused waveguide for delivering treatment electromagnetic radiation toward a target surface; U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S. Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled. Electromagnetically induced cutting with atomized fluid particles for dermatological applications; U.S. Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation; U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub, 20090225060 entitled Wrist-mounted laser with animated, page-based graphical user-interface; App. Pub. 20090143775 entitled Medical laser having controlled-temperature and sterilized fluid output; App. Pub. 20090141752 entitled Dual pulse-width medical laser with presets; App. Pub. 20090105707 entitled Drill and flavored fluid particles combination; App. Pub. 20090104580 entitled Fluid and pulsed energy output system; App. Pub. 20090076490 entitled Fiber tip fluid output device; App. Pub. 20090075229 entitled Probes and biofluids for treating and removing deposits from tissue surfaces; App. Pub. 20090067189 entitled Contra-angle rotating handpiece having tactile-feedback tip ferrule; App. Pub. 20090062779 entitled Methods for treating eye conditions with low-level light therapy; App. Pub. 20090056044 entitled Electromagnetic radiation emitting toothbrush and dentifrice system; App. Pub, 20090043364 entitled Electromagnetic energy distributions for Electromagnetically induced mechanical cutting; App. Pub. 20090042171 entitled Fluid controllable laser endodontic cleaning and disinfecting system; App. Pub. 20090035717 entitled Electromagnetic radiation emitting toothbrush and transparent dentifrice system; App. Pub. 20090031515 entitled Transparent dentifrice for use with electromagnetic radiation emitting toothbrush system; App. Pub. 20080317429 entitled Modified-output fiber optic tips; App. Pub. 20080276192 entitled Method and apparatus for controlling an electromagnetic energy output system; App. Pub. 20080240172 entitled Radiation emitting apparatus with spatially controllable output energy distributions; App. Pub. 20080221558 entitled Multiple fiber-type tissue treatment device and related method; App. Pub. 20080219629 entitled Modified-output fiber optic tips; App. Pub. 20080212624 entitled Dual pulse-width medical laser; App. Pub. 20080203280 entitled Target-close electromagnetic energy emitting device; App. Pub, 20080181278 entitled Electromagnetic energy output system; App. Pub. 20080181261 entitled Electromagnetic energy output system; App. Pub. 20080157690 entitled Electromagnetic energy distributions for electromagnetically induced mechanical cutting; App. Pub. 20080151953 entitled Electromagnet energy distributions for electromagnetically induced mechanical cutting; App. Pub. 20080138764 entitled Fluid and laser system; App. Pub. 20080125677 entitled Methods for treating hyperopia and presbyopia via, laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080069172 entitled. Electromagnetic energy distributions for electromagnetically induced mechanical cutting; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via, laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angel rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070128576 entitled Output attachments coded for use with electromagnetic-energy procedural device; App. Pub. 20070104419 entitled Fiber tip fluid output device; App. Pub, 20070060917 entitled High-efficiency, side-pumped diode laser system; App. Pub. 20070059660 entitled Device for dental care and whitening; App. Pub. 20070054236 entitled Device for dental care and whitening; App. Pub, 20070054235 entitled Device for dental care and whitening; App. Pub. 20070054233 entitled Device for dental care and whitening; App. Pub. 20070042315 entitled Visual feedback implements for electromagnetic energy output devices; App. Pub. 20070016176 entitled Laser handpiece architecture and methods; App. Pub. 20070014517 entitled Electromagnetic energy emitting device with increased spot size; App. Pub, 20070014322 entitled Electromagnetic energy distributions for electromagnetically induced mechanical cutting; App. Pub. 20070009856 entitled Device having activated textured surfaces for treating oral tissue; App. Pub, 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub, 20060241574 entitled Electromagnetic energy distributions for electromagnetically induced disruptive cutting; App. Pub. 20060240381 entitled Fluid conditioning system; App. Pub, 20060210228 entitled Fiber detector apparatus and related methods; App. Pub. 20060204203 entitled Radiation emitting apparatus with spatially controllable output energy distributions; App. Pub, 20060142745 entitled Dual pulse-width medical laser with presets; App. Pub. 20060142744 entitled Identification connector for a medical laser handpiece; App. Pub. 20060142743 entitled Medical laser having controlled-temperature and sterilized fluid output; App. Pub. 20060126680 entitled Dual pulse-width medical laser; App. Pub. 20060099548 entitled Caries detection using timing differentials between excitation and return pulses; App. Pub. 20060083466 entitled Fiber tip detector apparatus and related methods; App. Pub. 20060043903 entitled Electromagnetic energy distributions for electromagnetically induced mechanical cutting; App. Pub, 20050283143 entitled Tissue remover and method; App. Pub. 20050281887 entitled Fluid conditioning system; App. Pub. 20050281530 entitled Modified-output fiber optic tips; App. Pub. 20050256517 entitled Electromagnetically induced treatment devices and methods; App. Pub. 20050256516 entitled Illumination device and related methods; App. Pub, 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled Electromagnetic energy distributions for electromagnetically induced mechanical cutting.

All of the contents of the preceding applications, materials, and referenced matters/content are incorporated herein by reference in their entireties. Although the disclosure herein refers to certain illustrated embodiments, it is to be understood that these embodiments have been presented by way of example rather than limitation. For example, any of the radiation/energy outputs (e.g., lasers), any of the fluid outputs (e.g., water outputs), and any conditioning agents, particles, agents, etc., and particulars or features thereof, or other features, including method steps and techniques, may be used with any other structure(s) and process described or referenced herein, in whole or in part, in any combination or permutation as a non-equivalent, separate, non-interchangeable aspect of this invention. Corresponding or related structure and methods specifically contemplated, disclosed, referenced and/or claimed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include: (I) any one or more parts of the above disclosed or referenced structure and methods and/or (II) subject matter of any one or more of the following claims and parts thereof, in any permutation and/or combination. The intent accompanying this disclosure is to have such embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention as limited only by the appended claims.

What is claimed is:

1. An apparatus using conditioned fluid to treat a tissue target, comprising:
    a fluid output pointed in a general direction of an interaction region, the fluid output being constructed to place conditioned fluid particles into the interaction region, the interaction region being defined at a location above the target and the conditioned fluid being compatible with the target;
    a flow-control cassette coupled to the fluid output and comprising a plurality of selectable passages coupled to pass the conditioned fluid with different flow rates; and
    an electromagnetic energy source pointed in a direction of the interaction region, the electromagnetic energy source being constructed to deliver into the interaction region a peak concentration of electromagnetic energy that is greater than a concentration of electromagnetic energy delivered onto the target, the electromagnetic energy having a wavelength which is substantially absorbed by the conditioned fluid in the interaction region, wherein the absorption of the electromagnetic energy by the conditioned fluid energizes the fluid causing the fluid to expand and wherein disruptive forces are imparted onto the target.

2. The apparatus of claim 1, wherein:
    the fluid output is constructed to continuously place conditioned fluid into the interaction region for so long as instructed by a user input while a fluid conditioning cartridge is coupled to the apparatus; and
    the fluid output is constructed to continuously place non-conditioned fluid into the interaction region for so long as instructed by a user input while the fluid conditioning cartridge is coupled to the apparatus; and
    the fluid output is constructed to continuously place non-conditioned fluid into the interaction region for so long as instructed by a user input while the fluid conditioning cartridge is coupled to the apparatus.

3. The apparatus of claim 1, wherein;
    the fluid output is constructed to continuously place conditioned fluid into the interaction region for so long as instructed by a user input while the fluid conditioning cartridge is coupled to the apparatus; and the fluid output is constructed to continuously place reduced-concentration conditioned fluid into the interaction region for so long as instructed by a user input while the fluid conditioning cartridge is coupled to the apparatus.

4. The apparatus of claim 1, wherein the fluid output is constructed to continuously place conditioned fluid into the interaction region for so long as a fluid conditioning cartridge is coupled to the apparatus.

5. The apparatus as set forth in claim 4, wherein the fluid conditioning cartridge injects a conditioning agent into a fluid, whereby a conditioned fluid is formed.

6. The apparatus as set forth in claim 5, wherein:

the conditioning agent is a disinfectant; and the conditioned fluid comprises a composition of the disinfectant that is suitable for use on the target in combination with the electromagnetic energy for generation of the disruptive forces.

7. The apparatus as set forth in claim 6, wherein the target comprises hard or soft tissue.

8. The apparatus as set forth in claim 5, wherein:

the fluid conditioning cartridge is a first fluid conditioning cartridge that injects conditioning agent into the fluid to form conditioned fluid having a first composition; and the fluid output is constructed to continuously output conditioned fluid having a second composition when a second fluid conditioning cartridge is coupled to the apparatus.

9. The apparatus as set forth in claim 8, wherein the second fluid conditioning cartridge injects conditioning agent into the fluid to form conditioned fluid having the second composition of the conditioning agent.

10. The apparatus as set forth in claim 9, wherein the conditioning agent is disinfectant, the first composition is a first concentration of disinfectant, and the second composition is a second concentration of disinfectant that is different than the first concentration of disinfectant.

11. The apparatus as set forth in claim 9, wherein the second composition has a discernible physical property that is greater than the same discernible physical property of the first composition.

12. The apparatus as set forth in claim 11, wherein the discernible physical property is concentration of conditioning agent.

13. The apparatus as set forth in claim 11, wherein:

the conditioning agent is a disinfectant; and the conditioned fluid comprises a composition of the disinfectant that is suitable for use on the target in combination with the electromagnetic energy for generation of the disruptive forces.

14. The apparatus as set forth in claim 8, wherein the second fluid conditioning cartridge is constructed to be coupled to the apparatus in place of the first fluid conditioning cartridge.

15. The apparatus as set forth in claim 9, wherein:

the fluid conditioning cartridge is a first fluid conditioning cartridge;

the fluid output is constructed to continuously output conditioned fluid having a first composition of disinfectant that is suitable for use on the target, when the first fluid conditioning cartridge is coupled to the apparatus; and the fluid output is constructed to continuously output conditioned fluid having a second composition of disinfectant that is suitable for disinfecting a supply line, when a second fluid conditioning cartridge is coupled to the apparatus.

16. The apparatus as set forth in claim 15, wherein the second fluid conditioning cartridge is constructed to be coupled to the apparatus in place of the first fluid conditioning cartridge.

17. The apparatus as set forth in claim 1$, wherein the second composition has a discernible physical property that is greater than the same discernible physical property of the first composition.

18. The apparatus as set forth in claim 17, wherein the discernible physical property is concentration of conditioning agent.

19. The apparatus as set forth in claim 1, and further comprising a fluid conditioning cartridge, the fluid conditioning cartridge being configured to inject a conditioning agent, whereby a conditioned fluid is formed.

20. The apparatus as set forth in claim wherein:

the conditioned fluid comprises a disinfectant; and a composition of the disinfectant within the conditioned fluid particles is suitable for use on the target in combination with the electromagnetic energy for generation of the disruptive forces.

21. The apparatus as set forth in claim 1, wherein the conditioned fluid comprises a sterile fluid.

22. The apparatus as set forth in claim 1, wherein the conditioned fluid comprises sterile water.

23. The apparatus as set forth in claim 1, wherein the conditioned fluid consists of a sterile fluid.

24. The apparatus as set forth in claim wherein the conditioned fluid consists of sterile water.

* * * * *